United States Patent
Dutkowski

(10) Patent No.: US 12,367,406 B2
(45) Date of Patent: *Jul. 22, 2025

(54) METHOD AND SYSTEM FOR ONTOLOGY-BASED DYNAMIC LEARNING AND KNOWLEDGE INTEGRATION FROM MEASUREMENT DATA AND TEXT

(71) Applicant: Data4Cure, Inc., Waltham, MA (US)

(72) Inventor: Janusz Jozef Dutkowski, Wellesley, MA (US)

(73) Assignee: Data4Cure, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/828,988

(22) Filed: Sep. 9, 2024

(65) Prior Publication Data

US 2025/0028984 A1   Jan. 23, 2025

Related U.S. Application Data

(63) Continuation of application No. 16/060,400, filed as application No. PCT/US2016/065437 on Dec. 7, 2016, now Pat. No. 12,086,723.

(60) Provisional application No. 62/264,319, filed on Dec. 7, 2015.

(51) Int. Cl.
*G06F 16/00* (2019.01)
*G06F 16/248* (2019.01)
*G06F 17/18* (2006.01)
*G06N 5/022* (2023.01)
*G06N 5/04* (2023.01)
*G06N 20/00* (2019.01)
*G06T 11/20* (2006.01)

(52) U.S. Cl.
CPC ............ *G06N 5/04* (2013.01); *G06F 16/248* (2019.01); *G06F 17/18* (2013.01); *G06N 5/022* (2013.01); *G06N 20/00* (2019.01); *G06T 11/206* (2013.01)

(58) Field of Classification Search
CPC ...... G06F 17/18; G06F 16/248; G06T 11/206; G06N 5/022; G06N 20/00; G06N 5/04; G16H 50/70; G16H 70/60
See application file for complete search history.

(56) References Cited

U.S. PATENT DOCUMENTS

2019/0057134 A1\*   2/2019   Akirav .................. G06F 16/245

\* cited by examiner

*Primary Examiner* — Yicun Wu
(74) *Attorney, Agent, or Firm* — Law Office of Andrei D Popovici, PC

(57) ABSTRACT

Ontology-based dynamic learning and knowledge integration are performed from measurement data and text. Relationships between entities and entity states are inferred from data, text, and user input. Searching, integrating, visualizing and comparing relations are used to extract domain-specific knowledge, particularly in bioinformatics.

23 Claims, 13 Drawing Sheets

METHOD AND SYSTEM FOR ONTOLOGY-BASED DYNAMIC LEARNING AND KNOWLEDGE INTEGRATION FROM MEASUREMENT DATA AND TEXT

CROSS-REFERENCE TO RELATED APPLICATIONS

The present application is a continuation of U.S. patent application Ser. No. 16/060,400, scheduled to issue on Sep. 10, 204 as U.S. Pat. No. 12,086,073, which is a 371 national stage of PCT Application No. PCT/US16/65437, filed Dec. 7, 2016, which claims the benefit of the filing of United States provisional utility patent application No. 62/264,319, filed Dec. 7, 2015, the disclosures of which are incorporated herein by reference in their entirety.

Any and all applications for which a foreign or domestic priority claim is identified in the PCT Request Form as filed with the present application are hereby incorporated by reference under 37 CFR 1.57.

BACKGROUND OF THE INVENTION

Field of the Invention

The present invention relates to data processing techniques, knowledge extraction techniques, machine learning, statistical analysis, ontologies, text-mining and knowledge management. The present invention also relates to bioinformatics, biomedical data analysis, extraction of biomedical knowledge from data and text, and updating knowledge using data.

Background

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Many expert systems rely on decision rules, facts or assertions that are manually curated by experts. Such systems are expensive to create and maintain. Natural language processing (NLP) systems can extract certain kinds of assertion directly from text. NLP systems scale well and are cost-effective but can only learn what has already been described in literature or other domain texts. Methods for statistical analysis of data and machine learning systems can often be applied to address many decision problems and learning tasks including those in biology and medicine. However, methods and systems are lacking that would allow to iteratively extract, integrate, store, and search over statistical relations or statistical or machine learning models derived using such methods. For example, it is currently challenging to store inferred statistical relations, integrate them in a common interface, search over them and automatically or semi-automatically compare them to each other or compare them to literature or expert knowledge. There is a large and rapidly growing body of data and text available in many disciplines, domains of knowledge and industry domains. There are however significant difficulties in translating the data to knowledge, reproducing results of statistical analysis, keeping track or results, data provenance, and reconciling data-driven insights with legacy knowledge. In particular, using machine learning, data mining and statistical methods big or otherwise complex datasets can be used to generate a large number of models and hypothesis. In many areas of industry or domains of knowledge millions of models are being built or can be built in the near future. New data is often coming in continuously, both internal data within an organization and external data, providing the need update old models and build new ones. It is becoming increasingly hard to keep track of, reconcile, and understand such models or extract key insights that would be robust across many models. Often analysts within an organization may have access to only a limited set of models, and such analysts are often not aware of other models that might have been built using the same or different data or methods. Such other models may point to different conclusions and may be useful to evaluate in reference to the original models that an analyst may have access to. At the same time it is known that integrating multiple models and evidence types often leads to superior results in model accuracy and predictive ability. It may be highly beneficial to build new knowledge bases that are capable of storing and integrating the results of statistical or machine learning models, integrating such results and cross-referencing them with other information on a continuous basis, and allowing the user to search and view the integrated and cross-referenced results.

While this application provides examples of construction and uses of such knowledge bases in certain domains, it should be clear that many of the techniques described herein are and will be applicable to other types of structured data and text and to other domains of knowledge in science and industry. Uses of techniques described herein may include, without limitation, data analyses in the field natural language processing, biological and medical research, social sciences, financial data, historical and comparative linguistics, marketing research, forensics, social network analysis, fraud and crime detection and prevention.

DEFINITIONS

Figure 1:
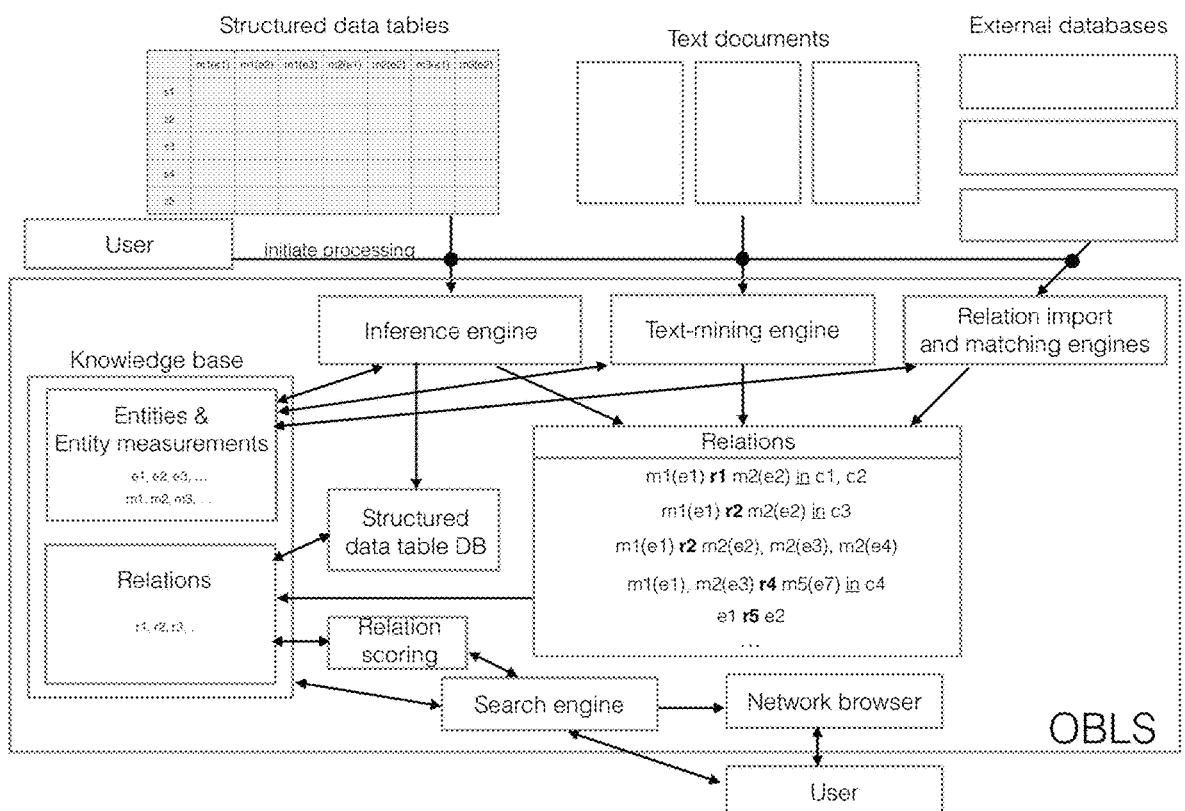
FIG. 1 is a schematic diagram showing an embodiment of an ontology-based learning system.

An "entity" is a something that exists in itself, actually or potentially, concretely or abstractly, physically or not that may be of interest to be represented in an ontology or an ontology-based learning system as contemplated here.

An "entity measurement" is a property or a measurable or observable state of an entity. The property or state may be constant or dynamic.

A "relation" is a set of entities or entity measurements each of which can have a specified role in the relation. Relations as contemplated here may be annotated with additional metadata, for example, a relation type, method used to derive the relation, data used to derive the relation, relation contexts, the direction of the correlation encoded in the relation, or other metadata that is helpful to understand and fully define the relation.

A "multivariate relation" as contemplated here is a relation with more than two entities or entity measurements.

A "relation role" is a specified position, for example a side of the relation, or an associated meaning or both a position and an associated meaning that an entity or entity measurement has in a relation.

An "ontology" is a set of entities, a set of entity measurements and a set of relationships between entities and/or entity measurements.

A "literature relation" or "text relation" refers to the relation that is mined from a corpus of texts or literature. Such relations are typically identified between two or more entities by identifying references to such entities that jointly appear in the same texts or literature, or that appear in common sentences, or appear jointly in specific textual contexts.

A "statistical relation" or a "data-driven relation" is a relation derived from a statistical association or a statistical or a machine-learning model.

DETAILED DESCRIPTION OF THE PREFERRED EMBODIMENT

All patents, applications, published applications and other publications referred to herein are incorporated by reference for the referenced material and in their entireties. If a module or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the singular forms "a", "an", and "the" include plural references unless indicated otherwise, expressly or by context.

A "Context and State-aware, Dynamic and Data-driven Ontology" (or "CSDD Ontology") here refers an extendable set of entities and entity measurements and an extendable set of relationships between entities and/or entity measurements where relationships can be or have been known, observed, inferred from data, described in text, input by the users or otherwise obtained and may be further specific to a particular domain context. For example, a CSADD ontology provided in the field of biomedical information may include entities corresponding to, for example, genes, pathways, diseases, drugs, proteins, miRNA, mRNA, types of clinical outcomes (e.g. patient survival or response to treatment), and states or entity measurements relating to entities such as, for example, gene, protein or mRNA abundance, gene mutation, drug dose, administration or lack of administration of a drug, length of patient survival or response to treatment indicated by a categorical outcome (e.g. complete, partial or no response), or response to treatment measured as, for example, decrease in tumor size, or length of progression-free survival. Relations in such a CSADD may include relationships between concepts corresponding to entities such as relationships between proteins, relationships between transcription factors or target genes, relationships between genes and diseases. Relationships may also be defined between concepts representing entity measurements, such as, for example, relations denoting a correlation between expression of one gene and expression of another gene, relations relating a change in genomic sequence in one gene with expression of another gene, relationships between copy number change in one or more genes and overall patient survival time for a disease. Furthermore, relationships may be defined to be specific to one or more contexts such as biological or medical condition. For example, certain relations may only exist in a given tissue type, or may be specific to a particular disease, or biological species (a reference is made to the Examples below).

In other domains a CSADD ontology may be used to model relationships between domain entities and entity measurements in that domain. For example, in customer management systems a CSADD ontology can provide relationships between customers or relationships between customer actions such as for example relationships between purchasing an item and purchasing another item or between purchasing an item and total purchase value. CSADD may be used in domains related to forensics and intelligence to model relationship between persons or groups of people or between the involvement by such persons or groups of people in certain activities. Some entities can represent specific individuals, whereas other entities can represent groups of individuals. Entity measurements may represent the state of a person or group, or it may represent the level of certain activity or a certain other quantity or quality associated with a group or an individual. Relations can model relationships between individuals, groups, or between individuals and groups. Other relations can model relationships between measurable or observable qualities or quantities associated with individual or groups. Such relations can also be limited to specified contexts, for example a geographical or a temporary context, or a context defined by the role of an individual or group, their professions, or activities, or by a combination of such contexts.

Overview of CSADD Ontology-based learning system. In some embodiments, a CSADD Ontology-based learning system (OBLS) can be implemented for constructing, updating and managing a dynamic data-driven knowledge base. An OBLS may acquire new knowledge from structured and unstructured data in the form of relations between entities and/or entity measurements defined by an ontology and integrate such relations to update the knowledge base of relations. A reference is made to FIG. 1 which presents an overview of possible system modules and their configuration in an embodiment of OBLS. An OBLS may provide one or more engines for acquiring new relations from data such as a relation inference engine, a text-mining engine, and/or an engine for importing or mapping relations from user input or external sources. A relation inference engine may provide methods and techniques for inferring relations from structured data. A module which accesses a database or ontology of entities and entity measurements and identifies entities or entity measurement names or labels in the headers of structured data sources may be provided. A text-mining engine which accesses a database or ontology of entities and entity measurements may be provided to infer or mine the relations between entities or entity measurements from unstructured documents and texts. A relation import engine may allow input of relations directly from the user or import of relations from an external dataset or database. A user may initiate the inference of relations from data tables, relation mining from text or relation import, for example, by using a web browser interface or an API to cause the appropriate module to process selected input data. An OBLS may provide the ability to be configured to automatically initiate inference, text-mining or relation import, for example, whenever new data or relations become available. Relations can be inferred, extracted or imported and integrated in the relation database or knowledge base. If relations were inferred from data tables the structured data tables with columns annotated with entities or entity measurements can be stored in the database of data tables and cross-referenced with the relations by storing the information about the sources data table(s) on the relation. A relation scoring module may be provided to score the relations in the knowledge base based on their support in data, text or literature or based on the confidence of the external data sources from which an interaction was sourced. In a preferred embodiment, a relation search engine may be provided. A user may communicate with the search engine using, for example, a web browser interface or an API and may search for relations. The user may use the search engine to identify relations containing particular entities or entity measurements or relations annotated with a particular context or relations similar to a given relation. In some embodiments the search engine may communicate with a dynamic relation-scoring module which may update or refine relation scores based on user-provided parameters. In a preferred embodiment, a network browser for displaying relations might be provided allowing the user to display a graph or a hypergraph of selected relations from the knowledge base.

Figure 2:
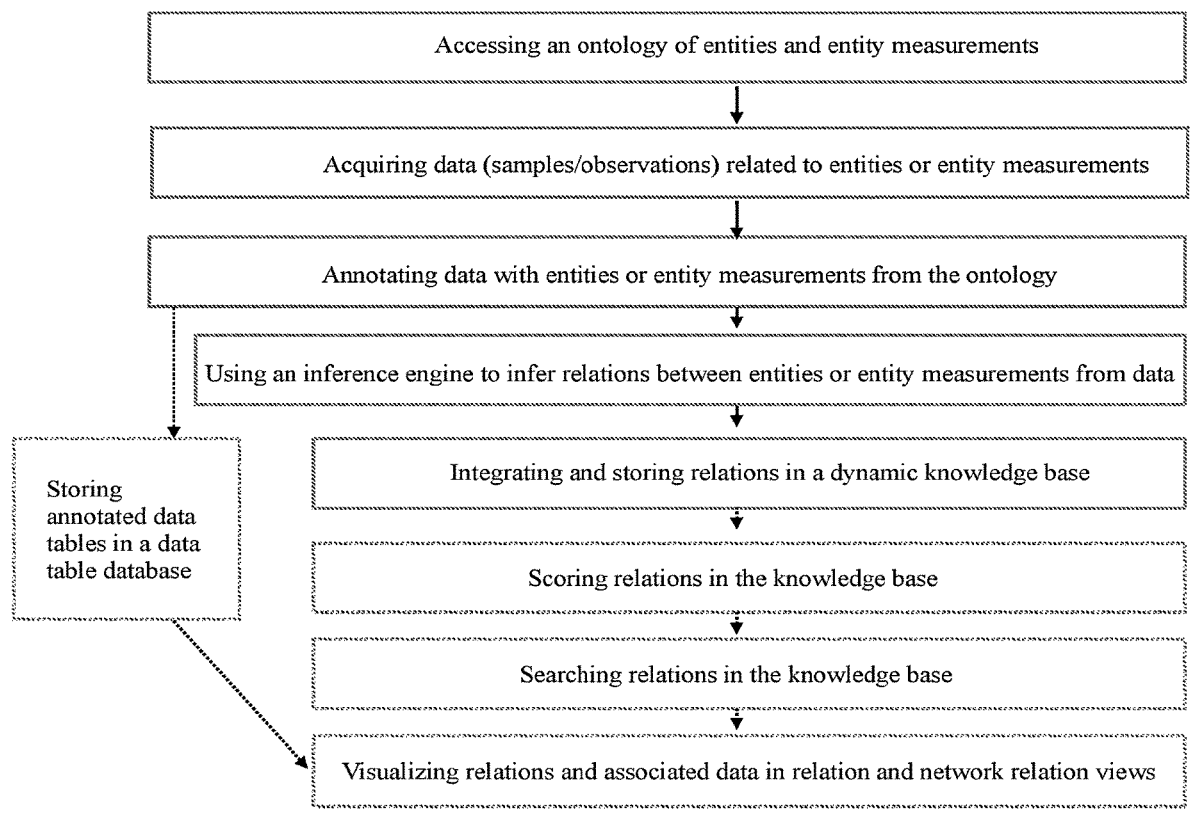
FIG. 2 is a schematic diagram showing an example of the process for creating and updating the knowledge base in an embodiment of an ontology-based learning system.

A reference is made to FIG. 2 which presents a schematic diagram of the process of constructing, updating a dynamic data-driven knowledge base. In some embodiments, an OBLS can provide a method for constructing, updating and managing a dynamic data-driven knowledge base comprising accessing an ontology of entities and entity measurements, acquiring data related to a plurality of entities or entity measurements, annotating the data with the entities or entity measurements from the ontology, using an inference engine to infer relations between entities or entity measurements from data, integrating relations between entities or entity measurements in an updatable data base of relations thus forming a dynamic knowledge base. In some embodiments, an OBLS may include an inference engine that implements one or more machine learning algorithms. In some embodiments, an OBLS may infer relations that are multivariate relations between more than two entities or entity measurements. In some embodiments, an OBLS may integrate relations in a graph or a hyper-graph structured database indexed by entities and entity measurements. In some embodiments, an OBLS may annotate or provide means to annotate relations with one or more context tags. In some embodiments, the database of relations may be further indexed by relation contexts. In some embodiments, an OBLS may provide a search engine that can be used to identify relations that contain particular entities, entity measurements or contexts, or relations that are similar to a given relation, or relations that meet user-specified criteria defined using filters. In some embodiments, an OBLS may provide a relation visualization engine that may be used to visualize the relation along with cross-referenced data from the data table database. In some embodiments, an OBLS may provide a module or modules for accessing textual data related to a plurality of entities or entity measurements, using a text-mining engine to derive relations between entities or entity measurements from text and integrating such text-derived relations between entities or entity measurements. In some embodiments, an OBLS may provide a scoring engine that is used to assign scores to relations. In some embodiments an OBLS may be configured to automatically or periodically perform inference of relations based on new data or new entities or entity measurements. In some embodiments, an OBLS may provide a module for data cleansing and formatting based on user-specified recipes. In some embodiments, an OBLS may enable storing the annotated data in a database that is cross-referenced with the relations. In some embodiments, an OBLS may provide a module accessing, formatting and importing relations from external data sources or based on recipes specified or configured by the user. In some embodiments, an OBLS may provide a module for importing relations specified by a user.

In a preferred embodiment, the invention provides a database for storing entities, entity measurements and relations.

In a preferred embodiment, the invention provides a method for scoring relations based on either support in data, support in text, confidence assigned by the users, or certain other criteria or a combination of such criteria. OBLS may provide a method to compute the relation scores dynamically when the user performs a search over the relation database or an OBLS may provide a method to precompute the relation scores either once or periodically and save the scores associated with the relations in a database. In some embodiments, an OBLS may further compute aggregate scores dynamically, for example to incorporate scores of other similar relations in the ontology.

In a preferred embodiment a relation browser may be provided. In a preferred embodiment a network relation browser may be implemented.

A reference is made to FIG. 1 which presents an overview of possible system modules and their configuration in a preferred embodiment. In some embodiments, a method for constructing, updating and managing a dynamic data-driven knowledge base is provided. In some embodiments, the method comprises accessing a database or entities, entity measurements and relations, using an inference engine to extract relations from data, storing relations in a database. In some embodiments, the method further comprises using a search engine to identify relations containing particular entities or entity measurements or relations similar to a given relation. In some embodiments, the method further comprises using a scoring engine to score relations in the knowledge base. In some embodiments the entities are biological or medical entities. In some embodiments the entity measurements pertain to biological or medical entities.

Figure 3:
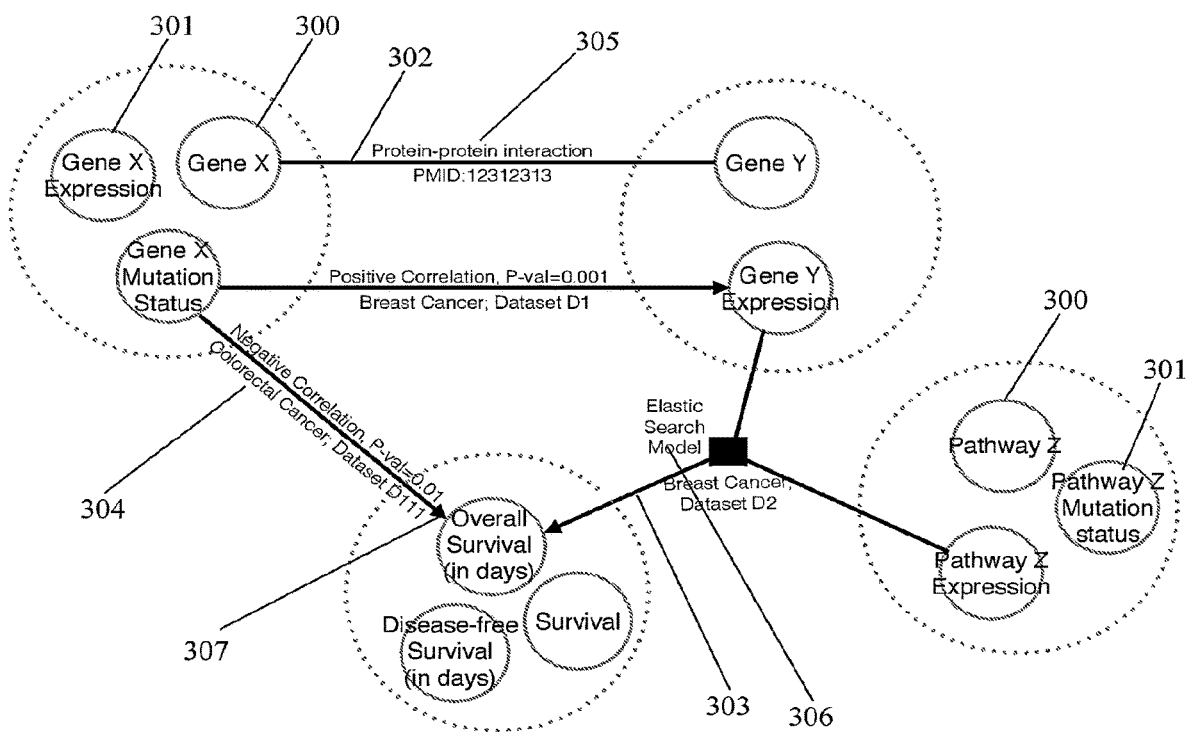
FIG. 3 provides an example structure of an ontology-based knowledge base.

In a preferred embodiment, a graph or a hypergraph structure can be used to integrate and represent the relations in the knowledge base. A reference is made to FIG. 3 which presents a schematic diagram of a hypergraph-structured knowledge base. Nodes in such a hypergraph may correspond to entities (100) or entity measurements (101). Edges (102) or hyperedges (103) correspond to relations or multivariate relations between entities or entity measurements. Relations may have assigned contexts (104) or additional parameters or metadata, such as relation type (105), the type of statistical test or model used to infer the relation (106), relation direction (107), or other parameters or metadata. In a preferred embodiment both entities and entity measurements can be indexed in the knowledge base providing the ability to search for either relations specific to a given entity measurement or all relations with a given entity, irrespective of the measurement. In some embodiments entity measurements may be hierarchically organized and entity measurements from multiple or all levels of the hierarchy may be indexed, providing the ability to represent and search for hierarchically-organized entities or entity measurements and their relations.

In some embodiments the inventions provides a method for storing the current entities and entity measurements and finding occurrences of entities and entity measurements in new structured and unstructured data or text or user inputs, or in imported documents, data tables, or relations, here jointly referred to as input data. A method can be implemented to identify the occurrences of entity or entity measurement names, labels or identifiers in the input data. The set of entities and entity measurements can also be extended dynamically. This can be done by automatic or user-informed transformation of structured data headers into entities and/or entity measurements. New entities and/or entity measurements can also be discovered from text, for example by mining for terms occurring frequently within a given text corpus. The system implementing the invention may provide the user with the ability to accept or reject new entities or entity measurement candidates discovered automatically. The system may also implement an interface to accept new entities and entity measurements from the user.

In a preferred embodiment, the invention provides a method to learn new relations based on the set of concepts in the ontology (corresponding to entities and entity measurements) by either inferring them from structured data, mining them from text, importing them from an external database or importing them from user input or other input data, or a combination of the above. In some embodiments, the system may be automatically or dynamically updated by initiating the computation, integration and storage of relations whenever new data is available or presented to the system. In some embodiments, the system may be dynamically updated by initiating the computation, integration and storage of relations, for example, when new entities or entity measurements are defined which could be identified in existing or new data available in the system. In some embodiments, the system may be dynamically updated by initiating the computation, integration and storage of relations, for example, when new ways of computing aggregate measurements are defined in the system.

Inference from data. In some embodiments a method for inferring new relations from data is provided. In some embodiments, the OBLS may access or be caused to access one or more data tables or data matrixes with rows corresponding to observations or samples that may contain observed values relating to one or more entities or entity measurements provided in an ontology. The column headers of a structured data table, formatted for instance as an SQL table, a comma-separated file or a tab-separated file, or a JSON, can be read and identified and mapped to the names, labels, or identifiers of a of entities or entity measurements in the ontology. The column headers of the structured data tables can be formatted in a way that facilities automatic mapping, for example, by structuring the names or identifiers of entities or entity measurements in a JSON format. In other embodiments, text-matching algorithms can be used to facilitate the matching of similar labels, names or identifiers, to map between the entities or entity measurements in the ontology and the column labels, names or identifiers in the data table. A semi-automatic procedure may be implemented that automatically identifies possible mappings based on text similarity or field matching, presents the possible mappings to the user and allows the user to select the preferred mapping or accept or reject a mapping or input a user specified mapping. Columns from one or multiple data tables can then be annotated with corresponding entities or entity measurements. New entities and/or entity measurements can be created if the column descriptors do not match existing entities or entity measurements. Data from columns matched with entities and/or entity measurements can then be used to infer relations between entities and/or entity measurements in the ontology, for example, using an inference engine.

An "inference engine," as described herein, refers to a software system that is designed to identify associations between two or more variables based on multiple samples or observations in which values for such variables are observed jointly or in a co—occurring or related fashion. An inference engine can be used to identify associations between two or more entity measurements based on the observed values encoded, for example, in columns of a data table where such columns are individually mapped to said entities or entity measurements. Statistical associations between entities or entity measurements can be represented as relations between said entities or entity measurements. Such relations can be stored in a system described here along with links to the data and any associated parameters or metadata that was used for or is related to the inference of such associations. In some embodiments described herein, an inference engine is provided, wherein the inference engine is used to identify significant associations between a plurality of entity measurements. Without being limiting, examples of inference engines can include systems which perform inference of statistical associations between variables or entity measurements. Associations can be identified by comparing the values of an entity measurement across multiple samples categorized by one of more conditions of interest where a condition may be determined based on the value of another entity measurement. For example, in some embodiments, associations may be identified by correlating the entity measurement values with a genomic or clinical trait, feature, measurement or observation that can be mapped to another entity or entity measurement in the ontology.

An inference engine might infer a relation between a certain condition denoted by the value of one entity measurement and the over-representation of certain values of another entity measurement. For example, an inference engine may compare samples or observations representing the events of certain gene mutation across two or more biological states to identify gene mutations that occurred in a particular state and then identifying the gene entities or entity measurements which have a significantly greater mutation frequency then expected at random, given the overall gene mutation frequency of the given biological condition. A binomial test, a hypergeometric test, or another relevant test known to those skilled in the art may be used to assess the overrepresentation of certain values within an entity measurement. Resulting statistical associations can be encoded as relations between entities or entity measurements corresponding to the biological condition and the gene mutation events. A biological state in the resulting inferred relations can also be encoded by a domain context and not specified directly as an entity measurement in the relation.

An inference engine might infer an association between an entity measurement having binary values and a real-valued entity measurement, by comparing the values of the real-valued entity measurement stratified using the binary value measurement using a statistical test such as at-test or Wilcoxon test or another test that can be used to compare a continuous variables across two conditions or two sets of samples. Such methods are known to those skilled in the art (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety). A reference is made to FIG. 4 which shows an example of a relation between a binary and a real-valued entity measurement.

An inference engine might infer an association between a real-valued entity measurement and a categorical entity measurement, for example, by comparing the data corresponding to the real-valued entity measurement stratified by the multiple values of the categorical measurement using a statistical test, such as, for example, an ANOVA test or another test used to compare the values of a continuous variable across multiple sets of samples known to those skilled in the art (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety).

An inference engine may infer associations be correlating the value of an entity measurement with patient or subject survival, using, for example, Cox regression analysis or another means for survival analysis or conditional survival analysis known to those skilled in the art (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety). A reference is made to FIG. 6 which shows an example of a relation in which cancer subtypes identified by molecular stratification are predictive of patient survival (604).

In some embodiments the invention provides means for representing, storing and relating entities or entity measurements pertaining to aggregate groups of other entities or entity measurements, e.g. groups of genes, pathways, biological complexes, groups of individuals, groups of products, or other such groups of entities or entity measurements that may be defined. In such cases, relations related to groups of entities can be inferred by analyzing entity measurements describing individual entities being part of the group. For example, an inference engine might implement a hypergeometric, or a gene set enrichment test to determine the association between a condition or state of one entity and the state of another entity representing molecular pathway, where the pathway's state is determined by many member genes whose activities or states are specified by individual gene-level entity measurements. In some preferred embodiments, a statistical test implemented by an inference engine may take into account the hierarchical structure of an ontology to provide more accurate scores and p-values, using one of the methods known in the field (for example, Grossmann et al.

Bioinformatics 2007, incorporated by reference in its entirety). In some embodiments scores can be defined, modified or influenced by the size of the aggregated set of entities or the scores of the parent, ancestor, children or descendant sets of entities in an ontology. In some embodiments, entity measurements corresponding to aggregate groups of entities can be precomputed and stored in the system as new entity measurements. Such precomputed entity measurements may be used to infer relations between other aggregated entity measurement or entity measurements pertaining to individual entities.

It will be known to those skilled in the art that other tests can be preferentially substituted and used to infer relations depending on the nature and distribution of the gene or module scores and the nature of the type of correlations or associations of interests.

It will also be understood that various covariates may be included while computing a statistical test to derive relations. For example, in some clinical applications covariates such as patient's age, gender, drugs or therapies administered to the patient, or overall tumor mutation frequency can be included in the analysis. Such covariates when used to infer relations may also be encoded and stored on the relation.

In a preferred embodiment, the inference engine may provide multivariate modeling and machine learning techniques and methods and systems for constructing classification models. In a preferred embodiment the results of some or all of such methods and techniques can be stored as relations. In some embodiments such relations may include multivariate relations. For example, a classification model can be trained based on the observed values of multiple discrete or real-valued entity measurements to predict another discrete-valued entity measurement. Machine learning and multivariate modeling techniques and methods for building classification models are known to those skilled in the art and can include, for example, decision trees, logistic regression, random forests, boosting decision trees, LDA, neural networks, deep learning (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety). From such a model a combination of a limited number of predictors being entity measurements may be extracted using feature scoring criteria, such as, for example recursive feature elimination, random forest feature importance measure, LASSO or Elastic Net regularization (Hastie, Tibshirani, Friedman, The Elements of Statistical Learning, 2009; Baldi, P. and Brunak, S. (2002). Bioinformatics: A Machine Learning Approach. Cambridge, MA:

MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press, incorporated by reference in its entirety). The predictive feature combination can be used to define a multivariate relation between the entity measurements corresponding to the top predictors in the model and the entity measurement corresponding to the predicted feature.

Figure 5:
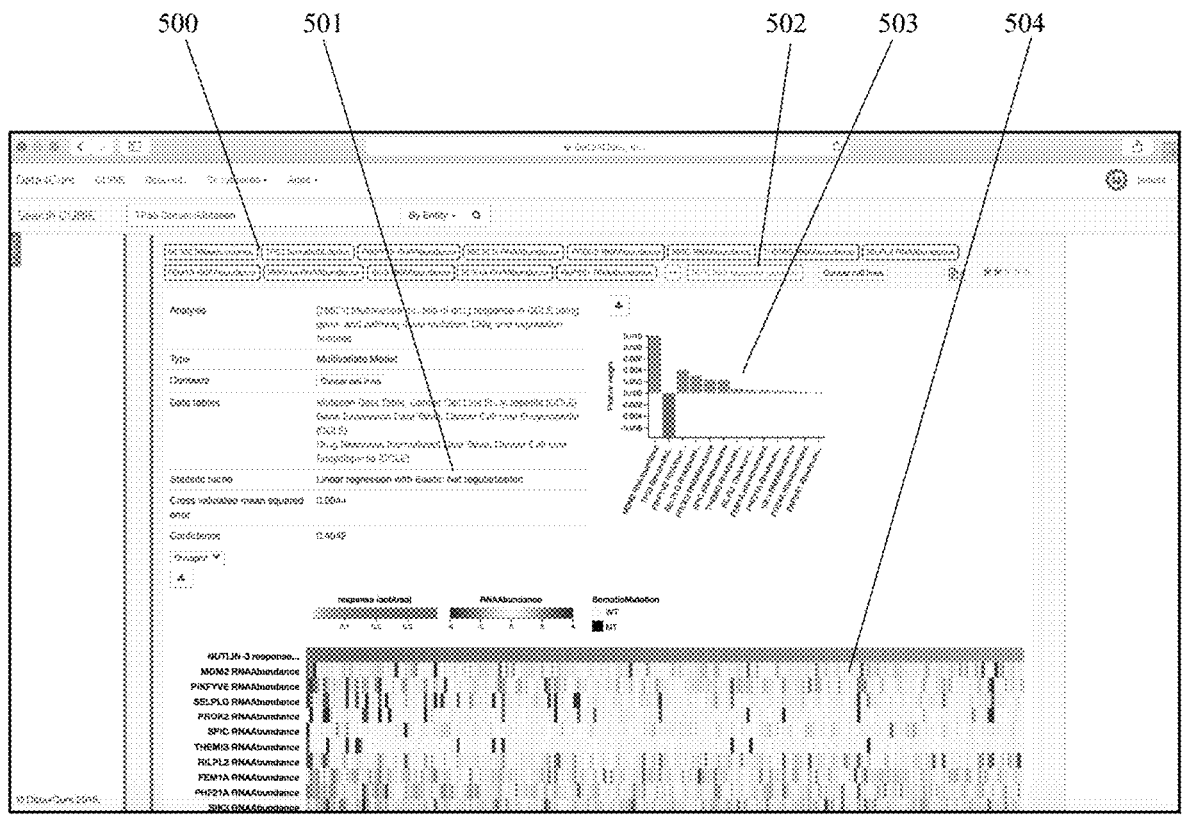
FIG. 5 shows an example of a relation details view for a multivariate relation.

In a preferred embodiment, the inference engine may provide multivariate modeling and machine learning techniques and methods and systems for constructing regression models. For example, a regression model can be trained based on the observed values of multiple discrete or real-valued entity measurements to predict another real-valued entity measurement. Methods for building regression models are known to those skilled in the art and include, for example, regression trees, linear regression, regularized regression such as lasso and elastic net, random forests, neural networks, and deep learning (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety). From such a model a combination of a limited number of predictors being entity measurements may be extracted using feature scoring and/or elimination criteria, such as, for example, recursive feature elimination, LASSO or Elastic Net regularization. The predictive feature combination can be used to define a multivariate relation between the entity measurements corresponding to the predictors in the model and the entity measurement corresponding to the predicted feature. Reference is made to FIG. 5 which depicts an example of a multivariate relation derived using an Elastic Net regression model, as specified by (501). In this example multiple entity measurements on the left-hand side of the relation (500) are together related to the entity measurement "Nutlin-3 Response (ActArea)"(502). The relative weights of the example top predictors in the model are plotted in (503). An example heatmap of the values of top predictors among the data samples is plotted in (504) and arranged according to the Nutlin-3 Response as measured in such samples.

In some embodiments, the inference engine may be used to infer multivariate models incorporating aggregate entity measurements pertaining to groups of entities. In some embodiments, the values of such aggregate entity measurements may be defined using hierarchical relationships between entities and entity groups that may be defined using an ontology. For example, in some embodiments, a binary entity measurement corresponding to the mutation status of a biological process (e.g. mutated or non-mutated) may be defined based on the mutation status of the genes associated with that biological process or the mutation status of a submodule of the biological process that may itself be a biological process or a protein complex or a pathway participating in the biological process. In some embodiments, a binary entity measurement corresponding to the mutation status of a pathway (e.g. mutated or non-mutated) may be defined as mutated if any of the genes in the pathway are mutated. In some embodiments, a binary entity measurement corresponding to the mutation status of a pathway (e.g. mutated or non-mutated) may be defined as mutated if a significant fraction of its genes are mutated. In some embodiments, a binary entity measurement corresponding to the mutation status of a pathway (e.g. mutated or non-mutated) may be defined as mutated if a significant fraction of its submodules are mutated. Regression, classifications, or other machine learning, statistical inference, and data-mining techniques may be applied to infer multivariate models incorporating aggregate entity measurements. From such a model a combination of a limited number of predictors being entity measurements may be extracted using feature scoring and/or elimination criteria, such as, for example recursive feature elimination, LASSO or Elastic Net regularization. The predictive feature combination can be used to define a multivariate relation between the entity measurements corresponding to the predictors in the model and the entity measurement corresponding to the predicted feature.

Figure 6:
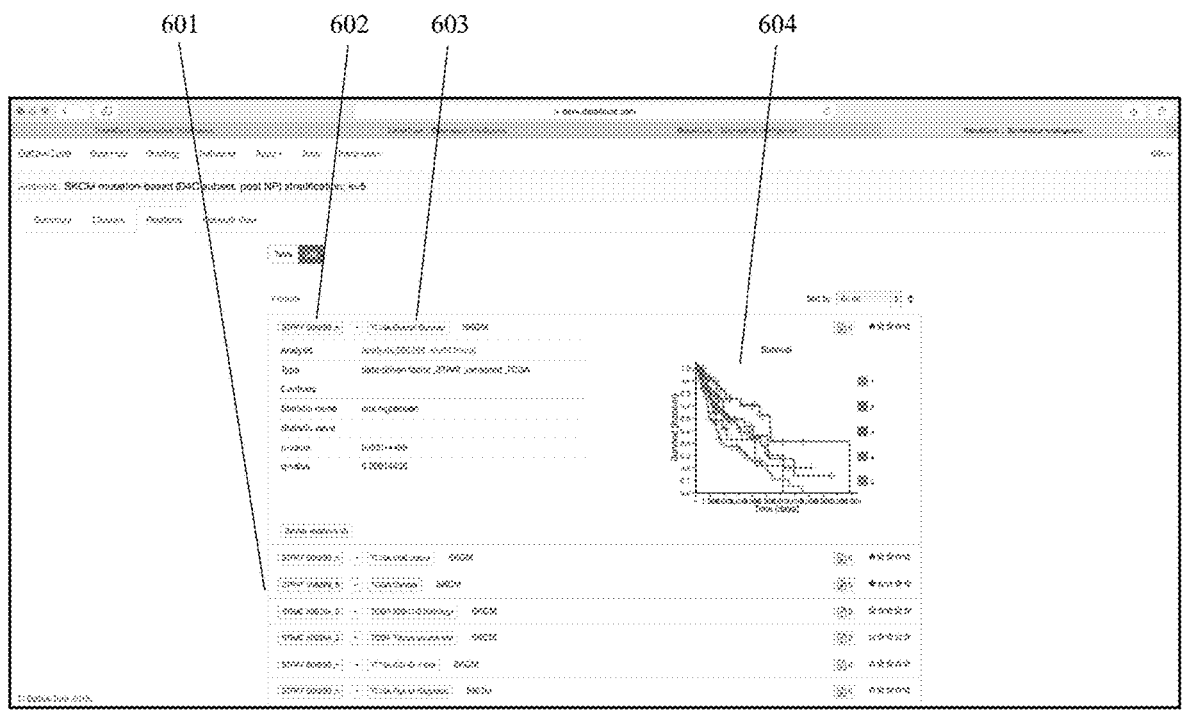
FIG. 6 shows an example of an analysis view for a clustering application and example relations resulting from the analysis.

Unsupervised learning or clustering methods may be applied to the observed values of multiple discrete or real-valued entity measurements to identify groups of samples with coherent entity measurement values or entity measurement values distinct from the values of those entity measurements in samples from other groups. Methods for clustering are known to those skilled in the art and include, for example, k-means, UPGMA, PAM, Non-Negative Matrix Factorization (NMF), model-based clustering and other clustering techniques (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety). Resulting sample partitioning may be correlated with other entity measurements. From such a model relations can be defined between entity measurements used for the clustering and any entity measurement that may be correlated with the clustering result. For example, in some embodiments relations may be inferred between patient survival or response to treatment and the assignment of samples to groups or clusters as defined by the clustering result. In some embodiments, a predictive feature combination predicting subtype assignment may be extracted and/or refined using feature selection, and/or elimination criteria, such as, for example recursive feature elimination, LASSO or Elastic Net regularization. The predictive feature combination can be used to define a multivariate relation between the entity measurements corresponding to the predictors in the model and the entity measurement corresponding to the predicted feature. Reference is made to FIG. 6 which depicts an example of a relation between a stratification assignment entity measurement (602) and certain clinical variables (601), including, for example, patient's overall survival (603).

In a preferred embodiment, a method or methods for mining relations from unstructured text can be implemented. Relations can be identified by mining for pairs of, or, more generally, for tuples of entities or entity measurements which co-exist within the same documents (Hastie, Tibshirani, Friedman, The Elements of Statistical Learning, 2009; Baldi, P. and Brunak, S. (2002). Bioinformatics: A Machine Learning Approach. Cambridge, MA: MIT Press; Baldi, P., Frasconi, P., Smyth, P. (2003). Modeling the Internet and the Web-Probabilistic Methods and Algorithms. New York: Wiley.; Cohen, P. R. (1995) Empirical Methods in Artificial Intelligence. Cambridge, MA: MIT Press. incorporated by reference in its entirety). Statistics such as, for example, the Jaccard index may be computed to score the propensity of two entities or entity measurements to co-exist within the same documents. Relations between entities or entity measurements with high Jaccard index can be defined as text relations between the corresponding entities or entity measurements. A Jaccard index can then be stored along with each such relation in the database and used to score that relation. It will be clear that other methods known to those skilled in the art may be used to infer certain specific types of relations from text such as, for example, directed regulatory relations between transcription factors and target genes. In some embodiments, additional constraints may be imposed on the occurrence of entities or entity measurements or their corresponding textual representations as recognized by text-mining methods. For example, co-occurrences of entities, entity measurements, or their representations may, in certain situations, only be considered if they occur in the same sentences, or within the same part of the text or within a specific textual context such as proceeded by, separated by, or followed by a specific text token, word or expression.

In a preferred embodiment an interface for integrating into the knowledge base manually entered relations from users can be provided. The invention may therefore allow the user to enter expert knowledge or manually-curated relations in the form of user-defined relations. In a preferred embodiment the interface can allow accessing lists of entities and entity measurements, relation types, or contexts to allow the user to easily define the relation to be integrated. In some embodiments the interface may allow for autocompleting the names of entities or entity measurements, relation types, or contexts as they are being specified by the user when defining a new relation to be integrated.

In a preferred embodiment, the invention may provide systems to ingest knowledge from external databases and systems by importing associations and transforming them to relations between entities or entity measurements in the ontology. For example, known and experimentally identified protein-protein, TF-DNA, and/or miRNA-RNA interactions from standard databases known to those skilled in the art can be imported as relations between corresponding entities in a biomedical ontology. Relation import modules may be implemented to import relations from external databases and systems. Rules can be defined that may be specific to external databases to allow for matching identifiers in external databases to entities or entity measurements in the ontology. Similarly, rules may be defined to allow for identifying relation types or contexts for new relations being imported. The system implementing the invention may provide an interface in which the user can review, approve, modify or reject relations in the knowledge base, relations inferred from data or text, or relations created or imported based on external knowledge.

Integration and storage of relations. In a preferred embodiment, relations inferred from data or text, or relations created or imported based on external knowledge can be stored in knowledge base or a database of relations. In some embodiments, relations may be filtered before integration into the knowledge base. For example, in some embodiments, it may be preferential to require that relations pass certain criteria to be stored in the database of relations, for example, that relations pass a score or a p-value threshold or certain other criteria that may be encoded in the system or specified by the user. In an embodiment the database of relations may be structured as a network and implemented, for example, using a graph database such as, for example, Neo4j, OrientDB Titan Virtuoso, GraphDb or another graph database. In a preferred embodiment the database of relations may be implemented in a NoSQL database, an RDF database or a database that can store JSON formatted data. In a preferred embodiment an indexing engine such as the Elastic Search engine may be used as part of the system to allow for fast retrieval of relations related to a particular entity or entity measurement or relations meeting selected criteria, for example criteria related to relation context or relation type. When a new relation is provided for storage it can be matched to existing relations by mapping corresponding entities or entity measurements across relations in order to find similar relations, that can be for example statistical relations, text relations, or user-defined relations, thereby identifying support for a new relationship based on relations present in the knowledge base that may be based on other data, literature, reference databases or prior knowledge. In a preferred embodiment relations can be stored with additional metadata such as, for example, pointers to the data table or data tables from which the relation was derived, or pointers to the text or body of literature from which the relation was derived, or pointers to the database or external data source or system from which the relation was imported. A relation defined on entities or entity measurements matching one or more columns of one or more tables can be indexed by the OBLS allowing the cross-referencing of the relation and the data, and providing a facility for the user to access the data associated with the relation or relations. In a preferred embodiment, the database of relations can allow easy identification of relations that are similar to other relations in the database in that they relate the same or largely the same entities or entity measurements. In a preferred embodiment, the database of relations can allow to find additional support for a relation by identifying relation that are similar. In a preferred embodiment, the database of relations can provide means to connect and integrate all relations by mapping the entities or entity measurements in the relations. Those skilled in the art will recognize that such a mapping may be implemented using a graph database where each entity or entity measurement is a node in the graph. In other preferred embodiments such a mapping may be implemented using a database utilizing RDF or JSON-formatted fields. Other databases such as SQL-based databases may also be used to implement such a mapping.

Figure 7:
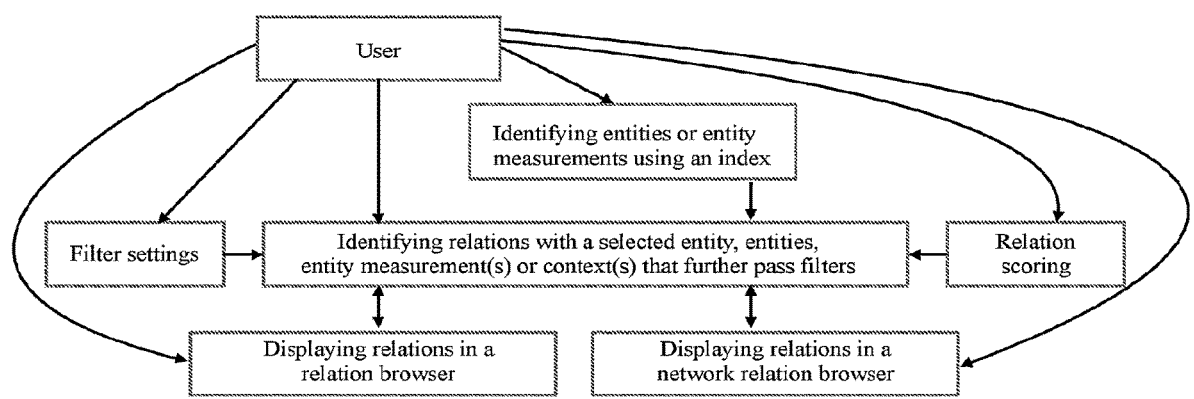
FIG. 7 is a schematic diagram showing an example of the process used for searching the knowledge base.

Search. In a preferred embodiment a search engine can be provided to allow the user to search for entities, entity measurements, relations, and/or contexts or other information that can be associated with entities or relations. A reference is made to FIG. 7 which provides a schematic diagram of an example search process that may be provided in an embodiment of the invention. In a preferred embodiment the search engine can index the entities by name, label, identifier, or description. In a preferred embodiment the search engine can index entity measurements by name, label, identifier, or description and by the name, label, identifier, or description of the entity. The search engine can also index other fields and metadata associated with entities, entity measurements or relation, for example fields specific to the entity measurements, relation contexts, relation types, or data sources from which relations were derived. In an example biomedical OBLS entity measurements can have various fields corresponding to for instance RNA abundance, protein abundance, protein, DNA, or RNA sequence mutation or variation, methylation, or other protein, gene, DNA, RNA, compound or drug dose, health condition, clinical parameters, environmental condition, or other molecular measurements and/or states. Such fields can be indexed for searching in some embodiments. Filters can be implemented to refine the search to entities from a certain name space or domain, entities, entity measurements or relations of a certain type or from a certain context. Search for relations can be either direct through accessing a relation index or indirect through first accessing entity or entity measurement index to identify the corresponding entities and entity measurements in the ontology, and then identifying relations pertaining to a certain entity or entity measurement(s). In a preferred embodiment, a user can specify a set of filters to filter relation search results by, for example, relation type, relation score, relation context or other parameters or characteristics that may be associated with relations. In a preferred embodiment, the relations resulting from a search can be sorted according to the values of relation scores or scores pertaining to relation classes and can be presented to the user in the order defined by the score. In a preferred embodiment, the search engine can rank the relations meeting the search criteria by the relation score. In some embodiments relation score may be modified by user settings to differentially weight score contributions such as, for example, support in data or support in a body of literature or support in reference databases. In a preferred embodiment, the search engine will provide a user interface, for example a web browser interface or an API to allow the user to specify search terms. In a preferred embodiment, the search engine interface may also allow the user to specify filtering or relation ranking parameters. In a preferred embodiment, the search results can be presented to the user in a relation browser. In a preferred embodiment, the search results may also be presented to the user in a network relation browser. A relation browser and/or a network relation browser may provide the ability to further refine or extend the search result through the use of the search engine.

Relation scoring. In a preferred embodiment a relation scoring mechanism can be implemented that takes into account scores, parameters or features directly associated with the relation being scored, as well as scores, parameters or features from other relations that are in the same relation class, or that are similar, for example those that relate to all or to a subset of the entities or entity measurements present in the relation. Such scores, parameters or features can be updated periodically, or each time a new similar relation is added or removed from the ontology. An aggregate function of scores, parameters or features from a relation and/or similar relations can be pre-computed for each relation and stored in the database or in the relation index to allow relation sorting. In a preferred embodiment the aggregate function can be computed at the time of query, when a user searches over the relation database. Being able to score and rank relations, for example by confidence, support in data or support in other similar relations is critical due to the very large number of possible relations in a data-driven knowledge base like the one contemplated here. In a preferred embodiment, the user may be provided with the ability to control the order of the relations resulting from a query by changing the parameters of the aggregation function to increase or decrease the impact of different input scores or pieces of evidence supporting the relation. A simple function of one of the parameters of features defined in the relations or an aggregate function of multiple such parameters or features can be used to define the relation score. For example, in some embodiments a score can be defined as a function of the p-value or the q-value of a statistical relation, or it can be defined as a function of the Jaccard score supporting a text relation. In a preferred embodiment a score for a relations can be defined as a function the parameters of the relation and parameters of all or some similar relations.

In some embodiments relations having many similar relations or many high-scoring similar relations will have high scores, thereby providing means to output to the user relations supported by multiple other relations that may be derived from multiple datasets, texts, or supported by multiple evidence or expert knowledge.

Figure 4:
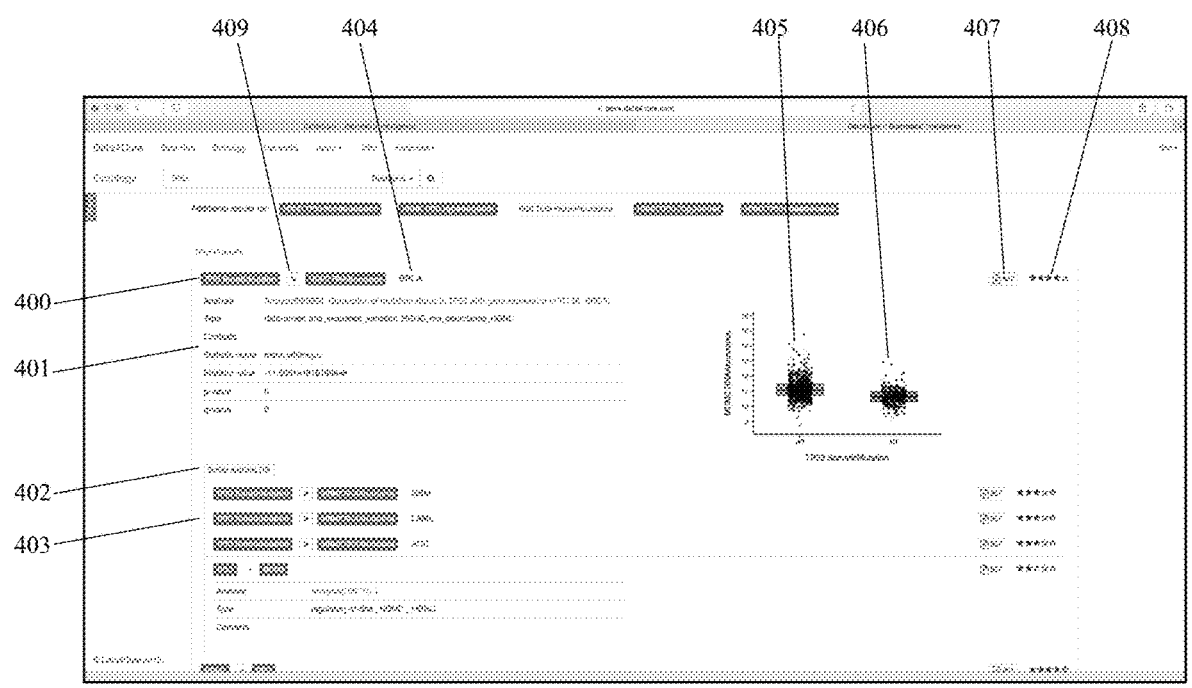
FIG. 4 shows an example of a search result and relation view featuring a data plot (boxplot), link to publications, and similar relations.

Displaying relations. In a preferred embodiment, the system implementing the method can present the user with additional information related to a relation. In a preferred embodiment the relation view as presented to the user in the user interface may contain identifiers of the entity and/or entity measurements in the relations, their role in the relation, relation contexts, pointers, identifiers or description of datasets or data sources used to derive the relation, one or more relations scores. In a preferred embodiment the relation view can also allow access to links or pointers to articles or documents in the literature which may support or may be relevant to the relation. In a preferred embodiment the relation view can also allow access to related relations in the ontology which relate the same entities or entity measurements as the relation being visualized or which are otherwise related to the displayed relation. In a preferred embodiment the system can automatically retrieve and present to the user all or a large part of the information related to the relation being visualized by querying the knowledgebase for similar relations, relations in the same class or relations with overlapping entities or entity measurements to the relation being visualized. In a preferred embodiment the relation view can also show plots, charts or tables displaying the data or a summary of the data supporting the relations. For a data-driven relation, in a preferred embodiment, the system can use the entities or entity measurements in the relation to identify and fetch appropriate columns from data tables that provided data values for inferring the relation. For a data-driven relation, in a preferred embodiment, the relation view may also show links or pointers to the statistical or machine learning analysis that generated the relation. In a preferred embodiment, the relation view can also show a relation confidence score or another quantitative or qualitative value that can be used to either rank or access the quality of the relation. Reference is made to FIGS. 4, 5 and 6 which provide examples of relation views.

Figure 8:
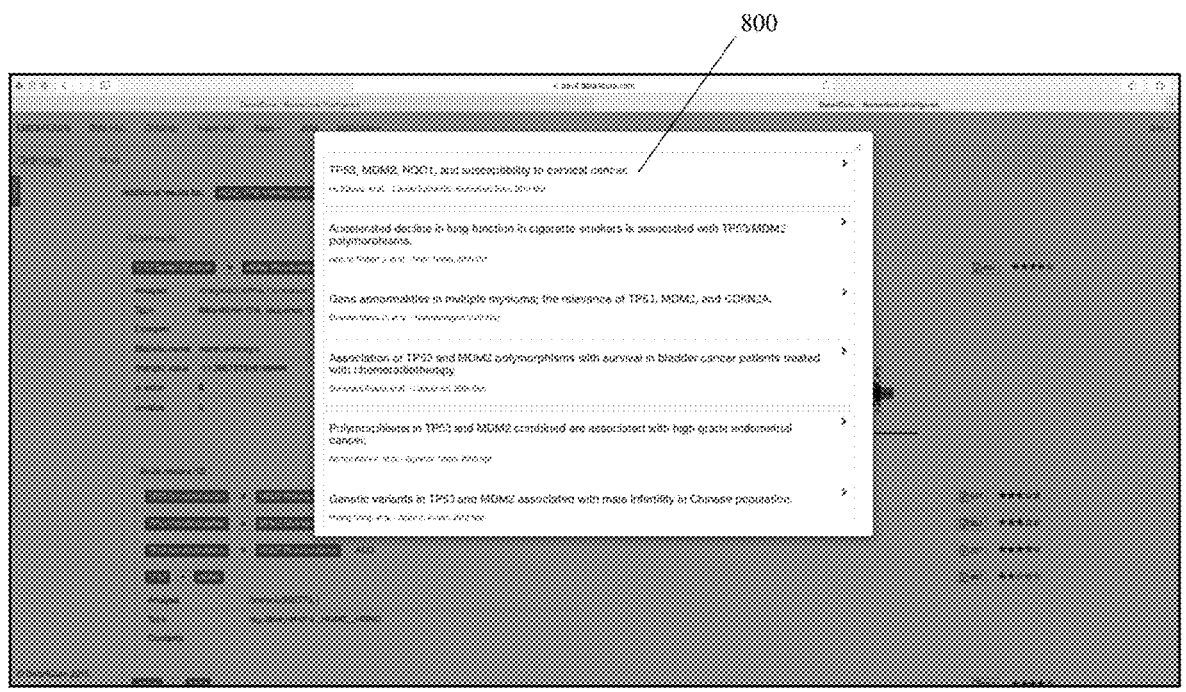
FIG. 8 shows an example of a related literature panel showing publications related to a relation.

Links to literature. In a preferred embodiment, the entity, entity measurement, or relation view as presented to the user by the system implementing the invention, may display links, pointers or direct quotations or extracts, or entire pieces of literature that support or inform about an entity or entity measurements or about the relation between entities or entity measurements contained in the relation. A reference is made to FIG. 8 which shows an example of a related literature panel showing publications related to a selected relation (800). The relevant pieces of literature or text, for example scientific papers, articles, biogs, textbooks, websites, etc. can be indexed using techniques known to those skilled in the art. The index may link the names, descriptions or identifiers of entities and/or entity measurements to pieces of literature or text which contain the given names, descriptions or identifiers, or which contain such names, descriptions or identifiers in a specific textual context, for example, contain the given names, descriptions or identifiers near each other in text. The pieces of literature or text which match all or some of the names, descriptions or identifiers may be retrieved based on such an index using techniques known to those skilled in the art.

Links to analysis results. In a preferred embodiment the relation view may provide links or pointers to an analysis view of the analysis that generated the relation displayed in the relation view. For example, all relations between an entity measurement corresponding to TP53 mutation and entity measurements corresponding to individual gene expression measurements may be identified in a single analysis. In this case, each such relation can point to the same analysis, allowing the user to compare such relations.

Finding similar relations. In a preferred embodiment, the system implementing the invention can enable the association of relations with other similar relations. The user may be shown similar relations or may be shown a link to similar relations within the relation view. Similar relations can be defined using different criteria which in some embodiments can be controlled by the user. For example, similar relations can be defined as those pertaining to the same set of entities or entity measurements. Similar relations can be defined as those sharing a non-empty subset of entities and/or entity measurements. In other embodiments, similar relations can be restricted to having the same entities and/or entity measurements in the same roles in the relations. Similar relations can be defined to have the same contexts or allowed to have different contexts. In a preferred embodiment, the system can allow to find additional support for a relation by identifying relations in the knowledge base that are similar to the said relation. For example, the system may identify relations that were imported from reference databases or relations that were mined from established literature and that support or are otherwise relate to a relation inferred from data. In a preferred embodiment, the system can provide means to connect and integrate all relations by mapping the entities or entity measurements in the relations. Such a system may utilize a graph database to implement such a mapping where each entity or entity measurement is a node in the graph. In other embodiments such a mapping may be implemented using a database utilizing RDF or JSON-formatted fields.

Grouping relations. In some embodiments, relations can be grouped into relation classes by grouping relations with the same or substantially the same entities or entity measurements. In some embodiments, relations may have to meet additional criteria, to be placed in the same relation class, such as, for example, having the same relation type, the same relation direction, or the same context. One relation from each class may be selected as a representative relation or a relation template may be created to represent the relation class. The relation search engine may allow filtering the relations to only return the representative relations for each group or only return relation classless, or only return individual relations. The system may compute aggregate scores for a relation class based on, for example, the number of class relations and the scores of individual relations in the class.

Network visualization. In a preferred embodiment, the invention may provide a network visualization component to display entities or entity measurements and relations between the entities or entity measurements. The network visualization component may additionally display data or additional information associated with entities, entity measurements, relations, analysis, data tables or data sources. Network nodes can represent either entities or entity measurements while edges can represent relations between entities or entity measurements. Hyper-graph edges (as exemplified in FIG. 3) may be used to represent multivariate relations. Entity measurements can be mapped to nodes corresponding to the entities specified in the entity measurements. Node colors can represent specific parameters from the relation originating or ending in a given node. For example, nodes corresponding to entity measurements whose values are positively correlated with the values of another entity or entity measurement in the relation can be assigned one color, whereas nodes corresponding to entity measurements negatively correlated with the values of the entity measurement can be assigned a different color. A reference is made to FIG. 11 where examples of node colorings and relations representations are provided (1105). Multiple types of queries may be implemented in the network browser. In one example, the network may display all relations from a given analysis. In another example, relations may be selected for visualization based on an entity or entity measurement that is part of the relation. In another example, relations which have all entities in a specified set of entities or entity measurements can be selected for visualization. In another example, relations of a specified type or context may be selected. In another example, a combination of the above criteria can be used to select the relations for visualization. In some embodiments, nodes can be assigned coordinates based on the entity or entity measurement or the type of entity or entity measurement they represent. In some embodiments nodes corresponding to entities can be connected to any or some relations which contain an entity measurement for that entity. In some embodiments, a node corresponding to entities or entity measurements can be extended by adding relations containing the entity or entity measurement. In some embodiments a user may select a node to be extended and may additionally specify search and filtering criteria for identifying relations to be added to the network as a subset of all relations containing the entity or entity measurement specified by the node. In some embodiments some or all of the nodes currently presented in the network display can be used to query for relations containing the entities or entity measurements represented by these nodes and such resulting relations can be used to expand the network.

EXAMPLES

Input data. The Broad GDAC Firehose provides publically-available preprocessed TCGA level 3 data and level 4 analyses packaged in a form amenable to immediate algorithmic intake (Marx, V. et al. *Nat. Methods* 10, 293-297 (2013); incorporated by reference in its entirety). From this resource gene mutations, copy-number variants, mRNA expression levels (microarray and RNAseq), and DNA methylation profiles were obtained for human subjects as well as selected clinical data such as overall patient survival, disease stage, histopathological type, the list of administered oncology drugs for each patient were also obtained, and selected other variables available in TCGA.

Molecular interaction networks, pathways, processes and components were obtained from publicly available databases. A human protein-protein interaction network was obtained from BioGRID (Stark, C. et al. *Nucleic Acids Res.* 39, D698-D704 (2011); incorporated by reference in its entirety), a functional gene interaction network HumanNet (Lee, I. et al. *Genome Res.* 21, 1109-1121 (2011); incorporated by reference in its entirety) was also obtained. A comprehensive collection of manually curated pathways from Pathway Commons (Cerami, E. G. et al. *Nucleic Acids Res.* 39, D685-D690 (2011); hereby incorporated by reference in its entirety). Static hierarchical ontologies of cellular components, biological processes and molecular functions from the Gene Ontology and the REACTOME database (Ashbumer, M. et al. *Nat. Genet.* 25, 25-29 (2000), Croft, D. et al. *Nucleic Acids Res.* 39, D691-D697 (2011), Ashbumer, M. et al. *Nat. Genet.* 25, 25-29 (2000); hereby incorporated by reference in its entirety). A human regulatory network was also compiled from the available ENCODE TF-DNA interactions and selected other manually curated resources.

Abstracts and bibliographical information for biomedical publications were downloaded from the PubMed database. Gene-drug interactions were obtained from an in-house manually curated resource.

Preparation of the ontology. Entities were defined corresponding to genes, pathways, processes, components, drugs, clinical outcomes, health conditions, and diseases. Examples of entities are provided as they can be encoded in the system:

Entity, Gene

```
{
    "type": "gene",
    "domain": {"name": "HGNC"},
    "name": "KRAS",
    "label": "KRAS"
}
```

Entity, Term

```
{
    "type": "term",
    "domain": {"name": "REACTOME"},
    "name": "REACT_121",
    "label": "Activation of PUMA and translocation to mitochondria"
}
```

Entity, Drug

```
{
    "type": "drug",
    "domain": {"name": "drug"},
    "name": "DACTINOMYCIN",
    "label": "DACTINOMYCIN"
}
```

Entity, Generic

```
{
    "domain": {"name": "TCGA"},
    "type": "generic_entity",
    "name": "Overall Survival",
    "label": "Overall Survival"
}
```

Entity, Health Condition

```
{
    "type": "health_condition",
    "domain": {"name": "TCGA health_condition"}, "name": "BRCA",
    "label": "BRCA"
}
```

Entity measurements were defined corresponding to gene mutation, gene expression, gene copy number variant, gene methylation, drug administration, and clinical parameters such as survival time, disease grade and stage, age, and other available clinical variables. Examples of entity measurements are provided as they can encoded in the system:

Entity measurement, Gene Mutation

```
{
    "label": "ABCA1 0 SomaticMutation",
    "entity": {
        "domain": {"name": "HGNC"},
        "type": "gene",
        "name": "ABCA10",
        "label": "ABCA10"
    },
    "modification": {
        "type": "dna_sequence_variation",
        "details": {"type": "somatic_mutation"}
    },
    "data_type": {
        "ordered": false,
```

-continued

```
        "levels": [
            {"value": 0, "label": "WT"},
            {"value": 1, "label": "MT"}
        ],
        "type": "numeric", "name": "factor"
    }
}
```

Entity measurement, Gene Copy Number Variation (CNV)

```
{
    "label": "ACAP3 CopyNumber",
    "entity": {
        "domain": {"name": "HGNC"},
        "type": "gene",
        "name": "ACAP3",
        "label": "ACAP3"
    },
    "abundance": "gene_abundance",
    "data_type": {
        "ordered": true,
        "levels": [
            {"value": 0, "label": "WT"},
            {"value": -1, "label": "HOM-LOSS"},
            {"value": -2, "label": "HET-LOSS"},
            {"value": +1, "label": "GAIN"},
            {"value": +2, "label": "MULTI-COPY-GAIN"}
        ],
        "type": "numeric",
        "name": "factor"
    }
}
```

Entity measurement, Gene Copy Number Gain

```
{
    "label": "TP53 CopyGain",
    "entity": {
        "domain": {"name": "HGNC"}, "type": "gene",
        "name": "TP53",
        "label": "TP53"
    },
    "abundance": "gene_abundance",
    "data_type": {
        "ordered": false,
        "levels": [
            {"value": 0, "label": "WT"},
            {"value": 1, "label": "GAIN"}
        ],
        "type": "numeric",
        "name": "factor"
    }
}
```

Entity measurement, Gene Copy Number Loss

```
{
    "label": "TP53 CopyLoss",
    "entity": {
        "domain": {"name": "HGNC"},
        "type": "gene",
        "name": "TP53",
        "label": "TP53"
    },
    "abundance": "gene_abundance",
    "data_type": {
        "ordered": false,
        "levels": [
            {"value": 0, "label": "WT"},
            {"value": 1, "label": "LOSS"}
        ],
        "type": "numeric",
        "name": "factor"
    }
}
```

Entity measurement, Gene Methylation

```
{
    "label": "A1BG Methylation",
    "entity": {
        "domain": {"name": "HGNC"},
        "type": "gene",
```

```
            "name": "AlBG",
            "label": "AlBG"
        },
        "modification": {
            "type": "epigenetic_modification",
            "details": {"type": "methylation"}
        },
        "data_type": {
            "type": "numeric",
            "name": "numeric"
        }
    }
```
Entity measurement, Gene Hypermethylation

```
{
    "label": "ARID1A Hypermethylation",
    "entity": {
        "domain": {"name": "HGNC"},
        "type": "gene",
        "name": "ARID1A",
        "label": "ARID1A"
    },
    "modification": {
        "type": "epigenetic_modification",
        "details": {"type": "methylation"}
    },
    "data_type": {
        "ordered": false,
        "levels": [
            {"value": 0, "label": "NORM"},
            {"value": 1, "label": "HMETH"},
        ],
        "type": "numeric",
        "name": "factor"
    }
}
```
Entity measurement, Gene Expression

```
{
    "label": "AlBG RNAAbundance",
    "entity": {
        "domain": {"name": "HGNC"},
        "type": "gene",
        "name": "AlBG",
        "label": "AlBG"
    },
    "abundance": "rna_abundance",
    "data_type": {
        "type": "numeric",
        "name": "numeric"
    }
}
```
Entity measurement, Generic Clinical

```
{
    "label": "VitalStatus",
    "entity": {
        "domain": {"name": "TCGA"},
        "type": "generic_entity",
        "name": "Vital status",
        "label": "Vital status"
    },
    "data_type": {
        "ordered": false,
        "levels": [
            {"value": "alive", "label": "alive"},
            {"value": "dead", "label": "dead"}
        ],
        "type": "character",
        "name": "factor"
    }
}
```
Entity measurement, Generic (drug treatment)

```
{
    "label": "DACTINOMYCIN Treatment",
    "entity": {
        "domain": {"name": "drug"},
        "type": "drug",
```

```
        "name": "DACTINOMYCIN",
        "label": "DACTINOMYCIN"
    },
    "data_type": {
        "ordered": false,
        "levels": [
            {"value": "Treatment", "label": "Treatment"},
            {"value": "Control", "label": "Control"}
        ],
        "type": "character",
        "name": "factor"
    }
}
```

A system module was implemented to reformat data tables to reference the entity measurements from a biomedical ontology that correspond to the measurements recorder in each column. For example, if an element in the table measured mRNA expression of gene X then the column header was formatted to reference the entity measurement corresponding to gene X mRNA expression. Similarly, mutation data was transformed to a tabular format where columns represented specific mutation events (i.e. whether or not there is a mutation in a gene or in one of the DNA regions), and rows corresponded to patient samples.

A system module was implemented to compute relations between entity measurements using the statistical test appropriate for each type of comparison. Relationships between either gene mutations, copy number changes or hypermethylation events and mRNA expression of other genes were computed using the Wilcoxon test, by comparing the expression in one group of samples (those with the event) to those in the other group of samples (those without the event). Cox regression analysis was used to associate gene mutations, copy number changes or hypermethylation events with differences in overall patient survival. Hypergeometric test was used to test whether a pathway, biological process, complex, function or other gene set contains more up or down regulated genes then expected by chance with respect to one of the events of gene mutations, copy number changes or hypermethylation, or treatment with a drug. ANOVA analysis was used to detect relations between categorical and continuous entity measurements. Significant associations identified by the system were transformed to relations between corresponding entity measurements retaining the corresponding score statistics, p-values, q-values, disease contexts and test types as relation parameters. Relations were grouped into analysis based on the event of interest. For example, an analysis was defined around all tests of individual gene expression changes associated with a mutation in TP53. Other analyses were defined to test other events (gene mutations, CNVs, and hypermethylation events for each gene, individually). Relations were further assigned the type "data-driven" and context based on the cancer they were identified in, for example breast cancer (BRCA) or lung adenocarcinoma (LUAD). Examples of relations derived from data are provided as they can be encoded in the system:

Relation, Gene copy number gain Enrichment (unary)

```
{
    "em1": null,
    "em2": {
        "table": "Data/TCGA/BLCA/cnv/cnv.tbl"
        "entity_measurement": {
```

```
            "label": "CDKAL1 CopyGain",
            "abundance": "gene_copy_gain",
            "entity": {
                    "domain": {"name": "HGNC"},
                    "type": "gene",
                    "name": "CDKAL1",
                    "label": "CDKAL1"
            }
    }
    "role": "response",
    "side": "right",
},
"directed": false,
"relation_direction": null,
"context": [{
        "entity": {
                "domain": {"name": "TCGA health_condition"},
                "type": "health_condition",
                "name": "BLCA", "label": "BLCA"
        }
}]
"attributes": {
        "p_value": 9.02284e-21,
        "q_value": 2.01958e-16,
        "stat_name": "binomial.test",
        "test_stat": null,
}
}
```

Relation, Gene Hypermethylation:Term Expression

```
{
"em1": {
    "table": "Data/TCGA/LAML/meth/meth.tbl",
    "entity_measurement": {
            "modification": {
                    "type": "epigenetic_modification",
                    "details": {"type": "hypermethylation"}
            },
            "label": "DPEP3 Hypermethylation",
            "entity": {
                    "domain": {"name": "HGNC"},
                    "type": "gene",
                    "name": "DPEP3",
                    "label": "DPEP3"
            }
    },
    "role": "predictor",
    "side": "left"
}
"em2": {
    "table": "Data/TCGA/LAML/rnaseq/NeXO_rnaseq.tbl",
    "entity_measurement": {
            "abundance": "rna_abundance",
            "label": "nucleosome organization
            RNAAbundance", "entity": {
                    "domain": {"name": "NeXO"},
                    "type": "term",
                    "name": "17740",
                    "label": "nucleosome organization"
            }
    },
    "role": "response",
    "side": "right"
}
"directed": true,
"relation_direction": "negative",
"context": [{
        "entity": {
                "domain": {"name": "TCGA health_condition"},
                "type": "health_condition",
                "name": "LAML",
                "label": "LAML"
        }
}]
"attributes": {
        "p_value": 1.58386422579e-16,
        "q_value": 1.1 9597587689e-12,
        "stat_name": "gsa.hypergeometric",
        "test_stat": null,
```

```
}
}
```

Relation, Gene Mutation:Generic Clinical

```
{
"em1": {
    "table": "Data/TCGA/LAML/mut/mut.tbl",
    "entity_measurement": {
            "modification": {
                    "type": "dna_sequence_variation",
                    "details": {"type": "somatic_mutation"}
            },
            "label": "NPM1 SomaticMutation",
            "entity": {
                    "domain": {"name": "HGNC"},
                    "type": "gene",
                    "name": "NPM1",
                    "label": "NPM1"
            }
    },
    "role": "predictor",
    "side": "left"
}
"em2": {
    "table": "Data/TCGA/LAML/clinical/clinical.tbl",
    "entity_measurement": {
            "entity": {"domain": {"name": "TCGA"},
            "type": "generic_entity",
            "name": "Overall Survival",
            "label": "Overall Survival"
    },
    "label": "OverallSurvival"
    },
    "role": "response",
    "side": "right"
}
"directed": true,
"relation_direction": "negative",
"context": [{
        "entity": {
                "domain": {"name": "TCGA health_condition"},
                "type": "health_condition",
                "name": "LAML",
                "label": "LAML"
        }
}]
"attributes": {
        "p_value": 3.6461e-05,
        "q_value": 0.000401071,
        "stat_name": "cox.regression",
        "test_stat": 124.572,
}
}
```

A system module was implemented to import physical protein-protein, functional and regulatory interactions as relations between gene or protein entities. Such interactions were transformed into either undirected (protein-protein and functional) or directed (regulatory) relations by identifying the entities corresponding to the genes or proteins in each interaction. Relations were assigned types, corresponding to networks from which they were derived, either "physical protein-protein", "regulatory", or "functional".

A system module was implemented to compute literature-based relations by searching for instances of entity names in all article abstracts available from PubMed. Relations were defined between pairs of entities which co-occurred in many abstracts as measured by the Jaccard Index. Other methods known to those skilled in the art can be employed to identify co-occurrence in text and extract relations between entities from a text corpus. A reverse-lookup index was used to search for occurrences of entities and entity measurements in article abstracts (Rafal Kuc, Marek Rogozinski, Mastering Elastic Search, 2013 PACKT, incorporated by reference in its entirety).

Entity and entity measurement indexes were constructed by creating a reverse index (Rafal Kuc, Marek Rogozinski, Mastering Elastic Search, 2013 PACKT, incorporated by reference in its entirety) from the names, synonyms, descriptions or measurement fields to the entities or entity measurements. Relation index was created by creating a reverse index from the names, synonyms, descriptions or measurement fields of entities and entity measurements to the relation fields (Rafal Kuc, Marek Rogozinski, Mastering Elastic Search, 2013 PACKT, incorporated by reference in its entirety).

Figure 9:
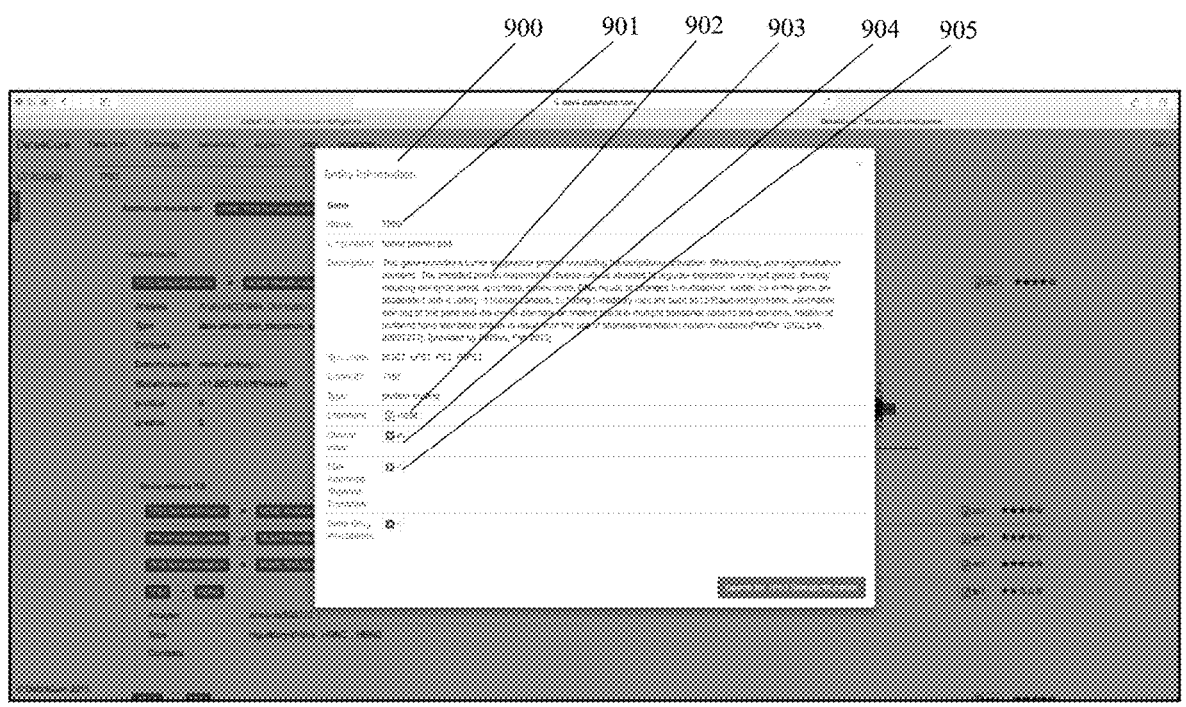
FIG. 9 shows an example of an entity details view with entity names, description, synonyms, links to related literature, clinical trials, and related drugs.

The system implementing the disclosed method can be used to identify relationships between entities and entity measurements. For example, in one of the embodiments described here, a search can be executed for the "TP53" gene [FIG. 4]. This search can yield hundreds of thousands of relations between the entity and entity measurements corresponding to "TP53" and other entities and entity measurements. For example, a relation may be returned between the entity measurement corresponding to TP53 somatic mutation (400) and MDM2 RNA abundance is depicted in FIG. 4. The exemplified relation is shown to have the "BRCA" context (404) and a high relation score (408). The statistics, p-value and q-value for the statistical association underlying this relation are depicted (401). A boxplot shows the relative expression of MDM2 among TP53 mutated (406) and wild-type (405) samples. From the relation view the user can access associated literature (407, a list of 857 publication abstracts may be accessed, see also FIG. 8) and 13 similar relations (403) including, for example, a regulatory relation between TP53 entity and MDM2 entity, as well as 12 other data-driven relations in different contexts (including GBM, LAML, ACC, and others). The functionality of "Similar relations" (402) in FIG. 4 can be useful for quickly identifying which relations found based on one dataset were also found based on other datasets, or in reference databases including protein-protein, regulatory and functional interactions. By clicking on the entity measurement button, for example the "TP53 SomaticMutation" button (400) depicted in FIG. 4, the user can access detailed information for the TP53 entity (900) in FIG. 9, including names (901), description (902), related literature (903), FDA approved drugs targeting the gene (905) and clinical trials referencing the gene (904).

Figure 10:
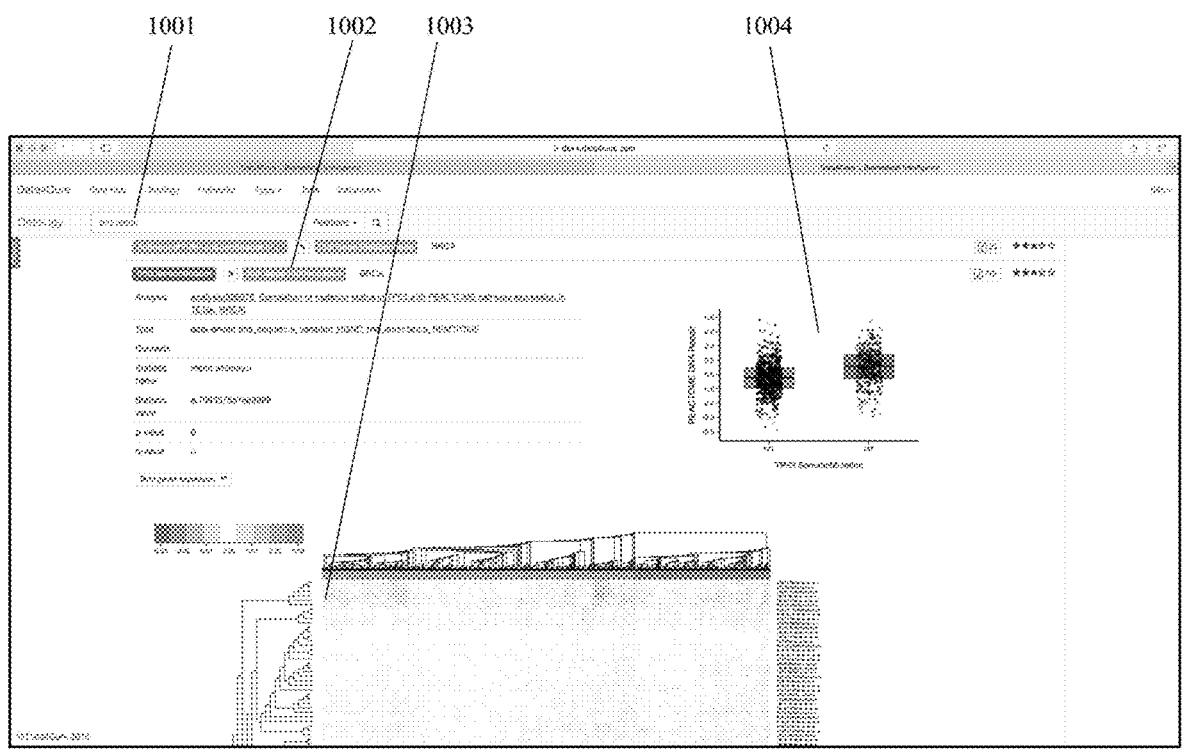
FIG. 10 shows an example of a relation details view with data plots (barplot and heatmap).

In one of the embodiments described here, the system can also be used to identify pathway relations. A reference is made to FIG. 10 which shows possible results of a search for "DNA repair" (1001). One of the relations in this example can be, for example, the relation between the entity measurements corresponding to TP53 somatic mutation and the REACTOME DNA Repair pathway RNA abundance (1002). An example of a heatmap (1003) is shown reporting the relative expression of the genes within the REACTOME DNA Repair pathway depending on the presence or absence of TP53 mutation in the corresponding samples (1004).

Figure 11:
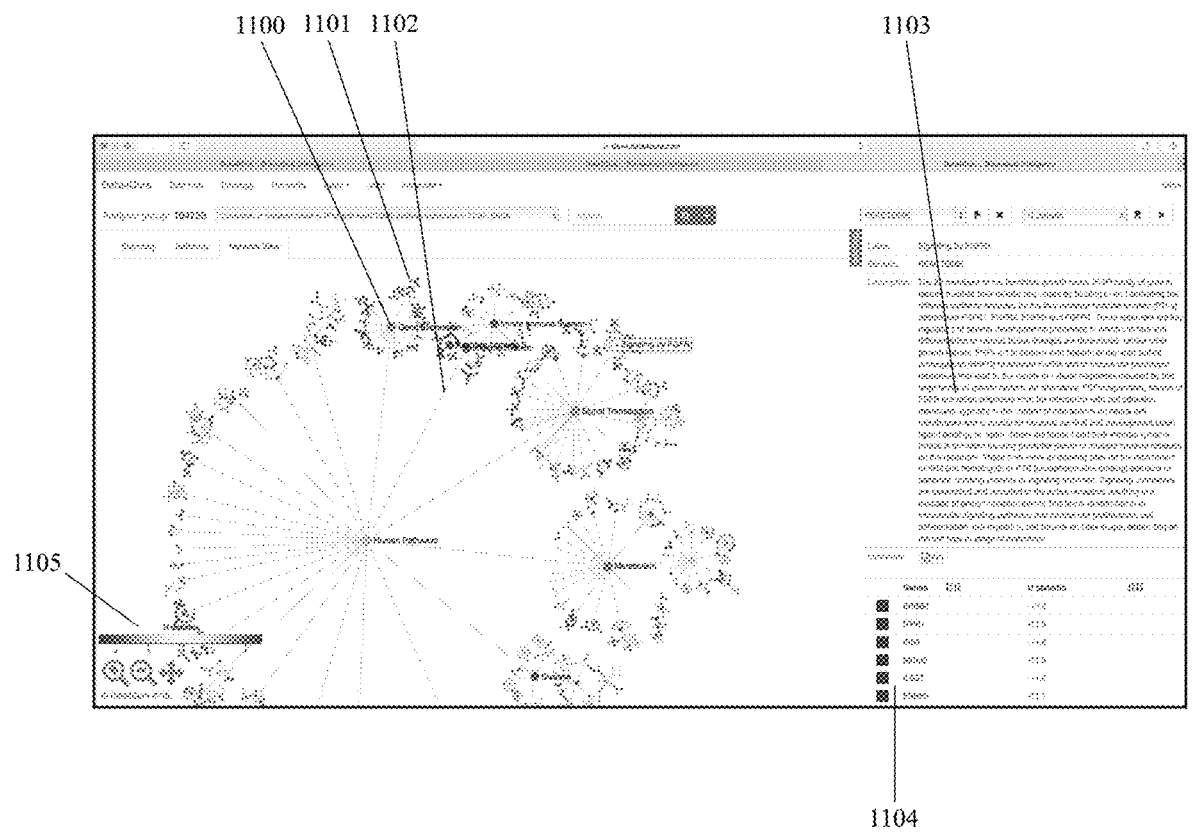
FIG. 11 shows an example of a network view with nodes corresponding to pathway entities and edges corresponding to parent-child relationships between the entities (i.e. that smaller pathway is contained within a larger pathway). Nodes may be further annotated with the change of expression of genes within each pathway, for example, either downregulated or upregulated.

The system, in one of the embodiments described here, can also be used to identify and analyze changes in activity across many pathways simultaneously. The example network view in FIG. 11 shows all REACTOME pathways with nodes corresponding to pathway entities and edges (1102) corresponding to parent-child relationships between the entities where a pathway represented by a smaller node (1101) is contained within a pathway represented by a larger node (1100). In this example, nodes may be colored according to the inferred change of expression of genes in association with TP53 mutation status within each pathway, either downregulated or upregulated (1105). The node details panel (1103) on the right hand side can provide information about the pathway entity and can also show the genes falling within this selected pathway and the corresponding gene-level gene expression relations (1104), in this example, relations with the TP53 mutation entity measurement.

Figure 12:
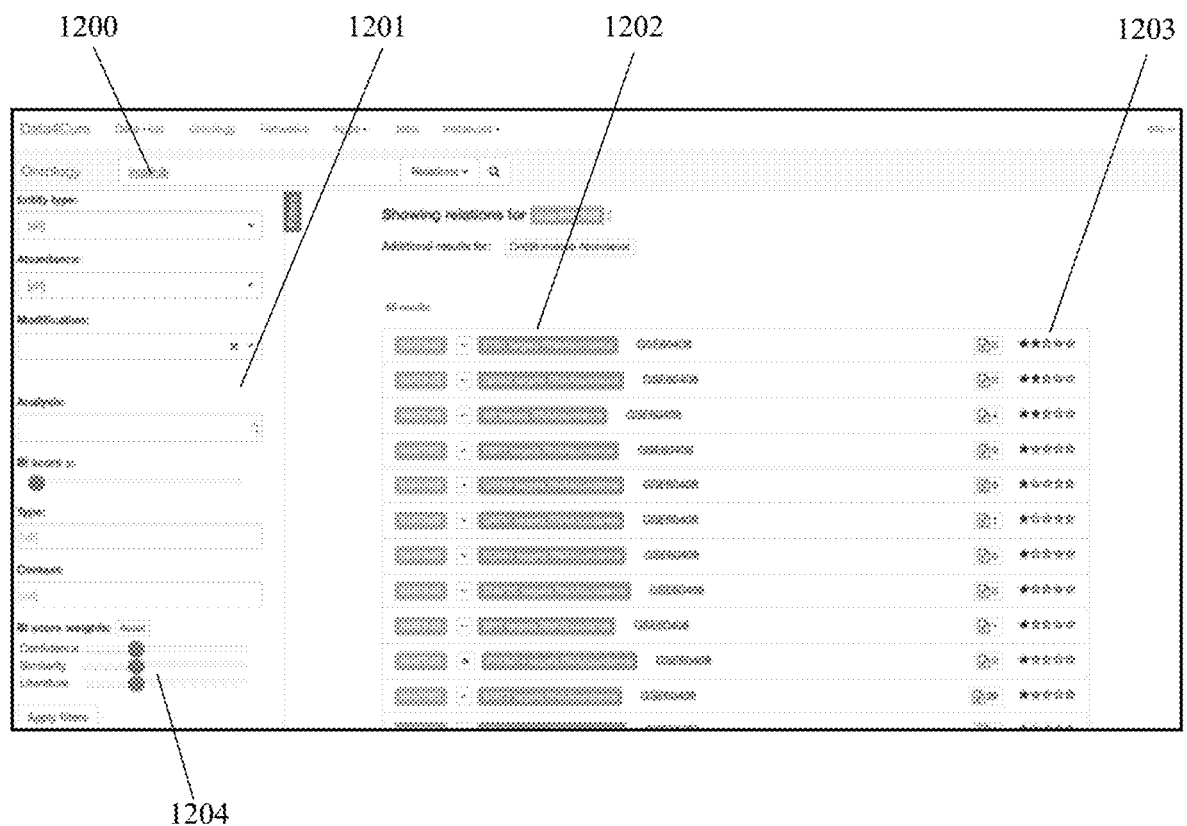
FIG. 12 shows an example of a drug relation search result and relation filters (left panel).
Figure 13:
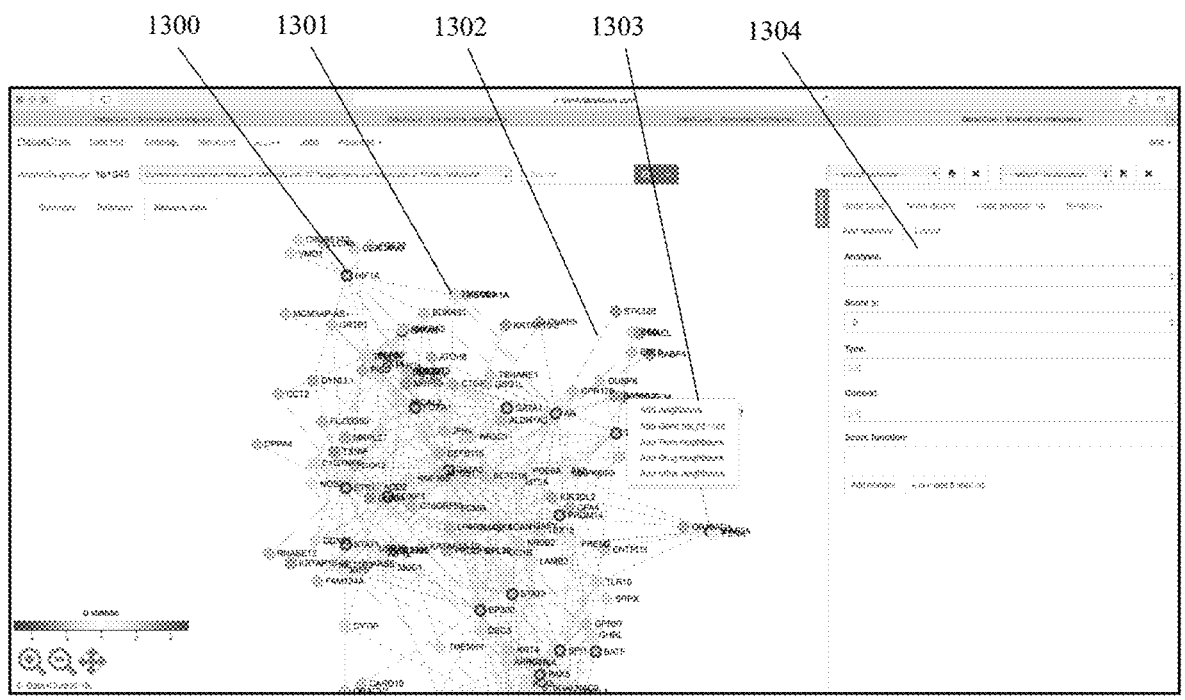
FIG. 13 shows an example of a regulatory network with transcription factors and downstream genes that may be further annotated, for example, according to the change in the expression of the gene associated with the even of drug treatment.

The system, in one of the embodiments described here, can also be used to identify drug relations. A reference is made to FIG. 12 which shows a possible result of a search for "imatinib" (1200) filtered to relations also involving transcription factor target sets. FIG. 13 shows and example of a regulatory network comprised of the transcription factors in the top-scoring relations with the entity measurement corresponding to treatment with Imatinib. The transcription factors in this example are represented by nodes with dark borders (1300). In this example, the remaining nodes correspond to the genes regulated by the transcription factors in the network (1301), as defined by regulatory relations (1302) from the ontology. Node colors may correspond to the statistic value from gene-level relations where the entity measurement corresponds to Imatinib treatment. The system may provide the user with the ability to add new relations and related entities or entity measurements to the existing network view. Examples of user interface menus for extending an existing node with new relations (1303) and adding other relations based on selected criteria are shown (1304).

The system may be used to identify a subset of the relations of an entity or an entity measurement or to identify the relations in a particular order according to the relation score. Examples of relation filters that may be implemented in an embodiment are provided in the right panel (1201) of FIG. 12 and may include entity name, type, and domain, or measurement filters for specifying the entity or entity measurement that must be present in a relation with an entity or an entity measurement specified in a query. Other filters may be used to select relations of a given type or with a score above a certain threshold. An aggregate relation score can be dynamically computed at the time of query based on the user-determined weights for each of the score components (1204). 1204 in FIG. 12 shows 3 sliding selectors for weights that in this example may correspond to q-value, literature co-occurrence as measured using the Jaccard index or the number of similar relations. Based on these weights a score 1203 can be computed for relations, for example, by weighting the contribution of each evidence type. Relations may be returned to the user in the order determined by the score, for example, by returning relations with the highest score first (1203).

Updates to the ontology. In a preferred embodiment the knowledge base of relations can be actively updated with relations resulting from new analyses. For example, FIG. 6 shows possible relations resulting from a mutation-based stratification analysis of the subcutaneous Melanoma (SKCM) TCGA cohort. In this example, the relations created in the system are between a new entity measurement (602) defining the partitioning of the samples resulting from the stratification and various clinical variables (601) that may be associated with the subjects being partitioned. Relations can be added dynamically to the ontology whenever a new analysis is executed and completed in the system. Such relations may comprise of existing entities and entity measurements, or entities or entity measurements created by the new analysis.

An embodiment of OBLS may be implemented to provide a data-driven knowledge base in many areas and applications which may include, without limitation, data analyses and knowledge base construction and maintenance in the field natural language processing, biological and medical research, social sciences, financial data, historical and comparative linguistics, marketing research, forensics, social network analysis, fraud and crime detection and prevention. An embodiment of OBLS may be used to model relationships between domain entities or entity measurements in a domain. For example, in customer management systems OBLS can provide relationships between customers or relationships between customer actions such as for example relationships between purchasing an item and purchasing another item or between purchasing an item and total purchase value. OBLS may be used in domains related to social network analysis or forensics or intelligence to model relationship between persons or groups of people or between the involvement by such persons or groups of people in certain activities. Some entities can represent specific individuals, whereas other entities can represent groups of individuals. Entity measurements may represent the state of a person or group, or it may represent the level of certain activity or a certain other quantity or quality associated with a group or an individual. Relations can model relationships between individuals, groups, or between individuals and groups. Other relations can model relationships between measurable or observable qualities or quantities associated with individual or groups. Such relations can also be limited to specified contexts, for example a geographical or a temporary context, or a context defined by the role of an individual or group, their professions, or activities, or by a combination of such contexts. OBLS may be used in financial or stock market analysis to model and construct and maintain a dynamic data-driven knowledge base of relationship between stock prices or various financial or market parameters, interest rates, foreign and domestic currency, prices of commodities, market trends and sentiments, or other market parameters and variables. OBLS may be used in commerce to build and provide a dynamic data-driven knowledge base of relationship between, for example, merchandise, merchandise prices, customer actions and buying habits, customer types, customer behaviors, competition, or other market parameters and variables.

The invention may provide a method for iterative learning and knowledge integration from measurement data comprising: accessing a database of entities, entity measurements and relations, using an inference engine to extract relations from data, storing relations in the database, using a search engine to identify relations containing particular entities or entity measurements or relations similar to a given relation.

The invention may provide a method for iterative learning and knowledge integration from measurement data and text comprising: accessing a database of entities, entity measurements and relations, using an inference engine to extract relations from data, using a text-mining engine for extracting relations from text, storing relations in the database, using a search engine to identify relations containing particular entities or entity measurements or relations similar to a given relation.

The invention may provide a method of relating the results of a statistical analysis to existing knowledge comprising accessing a dynamic ontology of entities, entity measurements and relations, using a search engine to identify relations containing particular entities or entity measurements or relations similar to relations identified in the statistical analysis.

The invention may provide a method for extracting and storing statistical relations between entities in the ontology and between entity measurements.

The invention may provide a method for extracting and storing literature relations between ontology entities and entity measurements.

The invention may provide a method for extracting and storing relations between measured states on ontology entities.

The invention may provide method for finding relations containing a particular entity or entity measurement.

The invention may provide method for storing and retrieving the results of a statistical analysis pertaining to ontology entities.

The invention may provide method of relating the results of a statistical analysis to relations extracted from literature.

The invention may provide a method for displaying relations on a network.

The invention may provide a method for finding similar relations.

The invention may provide a method for extending the network by additional relations adjacent to a network node(s).

The techniques described in this disclosure may be implemented in hardware, software, firmware, or combinations thereof. If implemented in software, the techniques may be realized at least in part by a computer-readable medium comprising instructions that, when executed, performs one or more of the methods described above. The computer-readable medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates code in the form of instructions or data structures and that can be accessed, read, and/or executed by a computer.

It is understood that the methods described herein may be implemented in one or more computers or network components. An embodiment of an OBLS system which may be implemented as a computer system, network system, data system or a computer implementing any or all components of the methods and systems described herein. The system can include one or more processors which communicate with input/output devices, a transmitter/receiver device and memory devices which may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The processor may be implemented using hardware or a combination of hardware and software. In an embodiment, the system may comprise of a relation inference module, data and relation import and integration module, relation search module, relation scoring modules, or data and relation visualization modules, any and all of which may be implemented in hardware or a combination of hardware and software including at least one processor.

The methods described herein can be implemented on any conventional host computer system, such as those based on Intel® or AMD® microprocessors and running LINUX, UNIX, OSX, or Microsoft Windows operating systems. Other systems, such as those using the UNIX or LINUX operating system and based on IBM®, DEC® or Motorola® microprocessors are also contemplated. The systems and methods described herein can be implemented to run on client-server systems and wide-area networks, such as the Internet.

Software to implement a method or model of the invention can be written in any well-known computer language, such as Python, Java Script, Java, C, C++, Visual Basic, FORTRAN or COBOL or a combination of such languages and where appropriate may be compiled using any well-known compatible compiler. The software of the invention normally runs from instructions stored in a memory on a host computer system. A memory or computer readable medium can be a hard disk, floppy disc, compact disc, DVD, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

The data matrices constructed by the methods described in this invention can be represented without limitation in a flat text file, in an SQL or noSQL database, graph database, RDF database, or in a markup language format including, for example, Standard Generalized Markup Language (SGML), Hypertext markup language (HTML), Extensible Markup language (XML) or JSON. Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, Learning XML O'Reilly and Associates, Sebastopol, CA (2001), incorporated by reference in its entirety.

A computer system of the invention can further include a user interface capable of receiving a representation of one or more relations, data tables, instructions, queries or reactions. It will be understood that a user interface may provide access to any or all of the components of the system described herein. A user interface can be implemented using as a web browser interface, a desktop interface, or an APL A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to the knowledge base described here, data table database, data and relation import modules, inference and text mining modules, relation search engine, relation filters, relation browser or relation network browser. The user interface can provide access to other databases useful in the invention such as other gene or protein networks, gene mutation data, a metabolic reaction database or links to other databases having information relevant to the reactions or reactants in the reaction network data structure or to human physiology. Also, the user interface can display a graphical representation of a dataset, a gene or protein network or another biological network or the results of the data analysis, stratification, clinical phenotypes or subtypes or subtype assignment derived using the invention.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. A computer system comprising at least one hardware processor configured to execute an inference engine, an integration engine connected to the inference engine and to a database, a relation scoring engine connected to the database, and a search engine connected to the database, wherein:

the database stores entity measurements defined by an ontology, wherein:

the ontology defines entities and entity measurements, each entity measurement characterizing a corresponding entity, the entities including biological entities and clinical entities, the entity measurements including biological entity measurements and clinical entity measurements, the biological entities include genes, proteins, drugs, mRNA, and/or biological pathways, the clinical entities include diseases and/or clinical outcomes, the biological entity measurements include measurements of genes, proteins, drugs, mRNA, and/or biological pathways, and the clinical entity measurements include measurements of diseases and/or clinical outcomes;

the inference engine is configured to infer a set of relationships between entity measurements from corresponding biological measurement data and clinical measurement data in the database, each relationship between entity measurements relating a biological entity measurement to a clinical entity measurement, each inferred relationship representing a statistical association between co-occurring biological entity and clinical entity measurements determined based on multiple samples or observations;

the integration engine is configured to update the database by adding the set of inferred relationships between entity measurements to a data structure including entity measurements and relationships between entity measurements;

the relation scoring engine is configured to generate a score for each inferred relationship, and to update the database with the generated scores; and the search engine is configured to query the database to identify responsive relationships between entity measurements in response to user queries including entity measurement identifiers.

2. The computer system of claim 1, wherein:

the inference engine is configured to infer a set of relationships between entities; and the integration engine is configured to update the database by adding the set inferred relationships between entities to the graph or hypergraph data structure, wherein the graph or hypergraph data structure further includes entities as nodes and relationships between entities as edges.

3. The computer system of claim 1, wherein the set of inferred relationships include multivariate relationships between more than two entity measurements.

4. The computer system of claim 1, wherein the set of inferred relationships include relationship directions.

5. The computer system of claim 1, wherein an inferred relationship between entity measurements includes a context tag characterizing a context of an inference of the relationship between entity measurements.

6. The computer system of claim 1, wherein the at least one hardware processor is configured to execute a text-mining engine connected to the integration engine and a set of text documents, and wherein:
  the text-mining engine is configured to mine text documents to identify relationships between entities; and
  the integration engine is configured to add relationships identified by the text-mining engine to the data structure including entity measurements and relationships between entity measurements.

7. The computer system of claim 1, wherein the at least one hardware processor is configured to execute a relationship scoring engine configured to generate scores for inferred relationships between entity measurements, the scores characterizing confidence in the inferred relationships.

8. The computer system of claim 1, wherein an inferred relationship between a biological entity measurement and a clinical entity measurement comprises:
  an identifier of a source in the database of data annotated with the biological entity measurement;
  an identifier of the biological entity measurement defined by the ontology;
  an identifier of a source in the database of data annotated with the clinical entity measurement; and
  an identifier of the clinical entity measurement defined by the ontology.

9. The computer system of claim 1, wherein the inferred relationship further comprises:
  a context tag characterizing a context of an inference of the relationship between entity measurements; and
  a set of attributes characterizing the inferred relationship, including a p value and a statistical test identifier characterizing a statistical test used to infer the relationship.

10. The computer system of claim 1, wherein the relation scoring engine is configured to generate the score for an inferred relationship according to parameters of the inferred relationship and according to parameters of relationships deemed similar to the inferred relationship.

11. The computer system of claim 1, further configured to group relations with the same entities or entity measurements into relation classes.

12. A method comprising employing at least one hardware processor of a computer system to:
  employ a database to store entity measurements defined by an ontology, wherein:
    the ontology defines entities and entity measurements, each entity measurement characterizing a corresponding entity, the entities including biological entities and clinical entities, the entity measurements including biological entity measurements and clinical entity measurements,
    the biological entities include genes, proteins, drugs, mRNA, and/or biological pathways,
    the clinical entities include diseases and/or clinical outcomes,
    the biological entity measurements include measurements of genes, proteins, drugs, mRNA, and/or biological pathways, and
    the clinical entity measurements include measurements of diseases and/or clinical outcomes;
  infer a set of relationships between entity measurements from corresponding biological measurement data and clinical measurement data in the database, each relationship between entity measurements relating a biological entity measurement to a clinical entity measurement, each inferred relationship representing a statistical association between co-occurring biological entity and clinical entity measurements determined based on multiple samples or observations;
  update the database by adding the set of inferred relationships between entity measurements to a data structure including entity measurements and relationships between entity measurements;
  update the database by adding a set of relationship scores, each relationship score generated for an inferred relationship; and
  query the database to identify responsive relationships between entity measurements in response to user queries including entity measurement identifiers.

13. The method of claim 12, wherein:
  the inference engine is configured to infer a set of relationships between entities; and
  the integration engine is configured to update the database by adding the set inferred relationships between entities to the graph or hypergraph data structure, wherein the graph or hypergraph data structure further includes entities as nodes and relationships between entities as edges.

14. The method of claim 12, wherein, wherein the set of inferred relationships include multivariate relationships between more than two entity measurements.

15. The method of claim 12, wherein the set of inferred relationships include relationship directions.

16. The method of claim 12, wherein an inferred relationship between entity measurements includes a context tag characterizing a context of an inference of the relationship between entity measurements.

17. The method of claim 12, wherein the method further comprises employing the at least one hardware processor of the computer system to:
  mine text documents to identify relationships between entities; and
  add identified relationships to the data structure including entity measurements and relationships between entity measurements.

18. The method of claim 12, wherein the method further comprises employing the at least one hardware processor of the computer system to generate scores for inferred relationships between entity measurements, the scores characterizing confidence in the inferred relationships.

19. The method of claim 12, wherein an inferred relationship between a biological entity measurement and a clinical entity measurement comprises:
  an identifier of a source in the database of data annotated with the biological entity measurement;
  an identifier of the biological entity measurement defined by the ontology;
  an identifier of a source in the database of data annotated with the clinical entity measurement; and
  an identifier of the clinical entity measurement defined by the ontology.

20. The method of claim 12, wherein the inferred relationship further comprises:
  a context tag characterizing a context of an inference of the relationship between entity measurements; and
  a set of attributes characterizing the inferred relationship, including a p value and a statistical test identifier characterizing a statistical test used to infer the relationship.

21. The method of claim 12, wherein a relationship score is generated for an inferred relationship according to parameters of the inferred relationship and according to parameters of relationships deemed similar to the inferred relationship.

22. The method of claim 12, further comprising grouping relations with the same entities or entity measurements into relation classes.

23. A non-transitory computer-readable medium storing instructions which, when executed by at least one hardware processor of a computer system causes the computer system to:
  employ a database to store entity measurements defined by an ontology, wherein:
    the ontology defines entities and entity measurements, each entity measurement characterizing a corresponding entity, the entities including biological entities and clinical entities, the entity measurements including biological entity measurements and clinical entity measurements,
    the biological entities include genes, proteins, drugs, mRNA, and/or biological pathways,
    the clinical entities include diseases and/or clinical outcomes,
    the biological entity measurements include measurements of genes, proteins, drugs, mRNA, and/or biological pathways, and
    the clinical entity measurements include measurements of diseases and/or clinical outcomes;
  infer a set of relationships between entity measurements from corresponding biological measurement data and clinical measurement data in the database, each relationship between entity measurements relating a biological entity measurement to a clinical entity measurement, each inferred relationship representing a statistical association between co-occurring biological entity and clinical entity measurements determined based on multiple samples or observations;
  update the database by adding the set of inferred relationships between entity measurements to a data structure including entity measurements and relationships between entity measurements;
  update the database by adding a set of relationship scores, each relationship score generated for an inferred relationship; and
  query the database to identify responsive relationships between entity measurements in response to user queries including entity measurement identifiers.

* * * * *